US009858665B2

(12) United States Patent
Metzger et al.

(10) Patent No.: US 9,858,665 B2
(45) Date of Patent: Jan. 2, 2018

(54) MEDICAL IMAGING DEVICE RENDERING PREDICTIVE PROSTATE CANCER VISUALIZATIONS USING QUANTITATIVE MULTIPARAMETRIC MRI MODELS

(71) Applicant: Regents of the University of Minnesota, Minneapolis, MN (US)

(72) Inventors: Gregory J. Metzger, Lake Elmo, MN (US); Stephen C. Schmechel, Seattle, WA (US); Chaitanya Kalavagunta, Crofton, MD (US); Joseph S. Koopmeiners, St. Paul, MN (US); Christopher A. Warlick, Lake Elmo, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 131 days.

(21) Appl. No.: 15/089,273

(22) Filed: Apr. 1, 2016

(65) Prior Publication Data

US 2016/0292855 A1    Oct. 6, 2016

Related U.S. Application Data

(60) Provisional application No. 62/142,815, filed on Apr. 3, 2015.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 5/055* (2013.01); *A61B 5/4381* (2013.01);
(Continued)

(58) Field of Classification Search
USPC ....... 382/100, 103, 106, 128–134, 153, 162, 382/168, 173, 181, 199, 203, 219, 224,
(Continued)

(56) References Cited

U.S. PATENT DOCUMENTS

| 6,004,267 A | 12/1999 | Tewari et al. |
| 7,245,748 B2 | 7/2007 | Degani et al. |

(Continued)

OTHER PUBLICATIONS

Kalavagunta, "Multiparametric MRI and Digital Pathology of Prostate Cancer, An Image Registration based Correlation Study," Nov. 2013; Donald Gleason Conference on Prostate and Urologic Cancers University of Minnesota, Department of Radiology, 1 pp.

(Continued)

*Primary Examiner* — Seyed Azarian
(74) *Attorney, Agent, or Firm* — Shumaker & Sieffert, P.A.

(57) ABSTRACT

A user-independent, quantitative, multiparametric MRI model is developed and validated on co-registered correlative histopathology, yielding improved performance for cancer detection over single parameter estimators. A computing device may be configured to receive a first parametric map that maps imaged tissue of a patient using values of a first parameter, and a second parametric map that maps the imaged tissue using values of a second parameter, wherein the parametric maps are generated from medical imaging data for the imaged tissue. The computing device may be further configured to apply a multiparametric model to the maps to generate at least one Composite Biomarker Score for the tissue, the model being a function of the first parameter and the second parameter. The function may be determined based on co-registered histopathology data. The computing device may be further configured to generate an indication of whether the tissue includes predicted cancer, and output the indication.

18 Claims, 9 Drawing Sheets

(51) Int. Cl.
 C40B 30/04 (2006.01)
 A61B 5/055 (2006.01)
 A61B 5/00 (2006.01)
(52) U.S. Cl.
 CPC . A61B 2576/02 (2013.01); G06T 2207/10088 (2013.01); G06T 2207/20081 (2013.01); G06T 2207/30024 (2013.01); G06T 2207/30081 (2013.01)
(58) Field of Classification Search
 USPC ....... 382/232, 254, 274, 276, 291, 305, 312; 506/9, 18; 378/21
 See application file for complete search history.

(56) References Cited

U.S. PATENT DOCUMENTS

| | | | |
|---|---|---|---|
| 7,831,293 | B2 | 11/2010 | Ellis et al. |
| 8,295,575 | B2 | 10/2012 | Feldman et al. |
| 8,386,012 | B2 | 2/2013 | Fehre et al. |
| 8,518,650 | B2 | 8/2013 | Mitchell et al. |
| 8,548,562 | B2 | 10/2013 | Trachtenberg et al. |
| 2008/0214950 | A1 | 9/2008 | Fehre et al. |
| 2010/0169024 | A1 | 7/2010 | Madabhushi et al. |
| 2013/0196868 | A1* | 8/2013 | Lebowitz ........... G01N 33/6893 506/9 |
| 2013/0287283 | A1* | 10/2013 | Kamath ................. G09G 5/026 382/133 |
| 2014/0073907 | A1 | 3/2014 | Kumar et al. |
| 2014/0185891 | A1* | 7/2014 | Schoenmeyer ....... G06T 7/0012 382/128 |
| 2014/0303041 | A1* | 10/2014 | Hayes .................... C07K 16/18 506/18 |
| 2015/0317431 | A1* | 11/2015 | Gronberg ............. C12Q 1/6886 506/9 |

OTHER PUBLICATIONS

Nam et al., "JPStitch 2.0: a Software for Volumetric Reconstruction and Analysis of Digitized Pathology," University of Minnesota, Nov. 2013; Donald Gleason Conference on Prostate and Urologic Cancers; Minneapolis, MN, 1 pp.
Kalavagunta et al., "Registration of In-vivo Prostate MRI and Pseudo Whole Mount Histology using Local Affine Transformation with Internal Structures (LATIS)," Proc. Intl. Soc. Mag. Reson. Med. vol. 20, 2012, 1 pp. (Applicant points out, in accordance with MPEP 609.04(a), that the year of publication, 2012, is sufficiently earlier than the effective U.S. filing date, Apr. 3, 2015, so that the particular month of publication is not in issue.).
Xiao et al., "Determining histology—MRI slice correspondences for defining MRI-based disease signatures of prostate cancer," Computerized Medical Imaging and Graphics, vol. 35, No. 7-8, Oct.-Dec. 2011, 11 pp.
Kalvagunta et la., "Pixel-Wise Multi-parametric Assessment of Prostate Cancer from Co-registered regions of Pathologically defined Disease," Proc. Intl. Soc. Mag. Reson. Med., vol. 22, 2014, 1 pp. (Applicant points out, in accordance with MPEP 609.04(a), that the year of publication, 2012, is sufficiently earlier than the effective U.S. filing date, Apr. 3, 2015, so that the particular month of publication is not in issue.).
Metzger et al., "Development of Multigene Expression Signature Maps at the Protein level from Digitized Immunohistochemistry Slides," PLos ONE, vol. 7, No. 3, Mar. 2012, 12 pp.
Metzger et al., "Detection and grading of prostate cancer using model-based spectral fitting," Proc. Intl. Soc. Mag. Reson. Med., vol. 22, 2014, 1 pp. (Applicant points out, in accordance with MPEP 609.04(a), that the year of publication, 2014, is sufficiently earlier than the effective U.S. filing date, Apr. 3, 2015, so that the particular month of publication is not in issue.).

Wilt, "The Prostate Cancer Intervention Versus Observation Trial:VA/NCI/AHRQ Cooperative Studies Program #407 (PIVOT): Design and Baseline Results of a Randomized Controlled Trial Comparing Radical Prostatectomy With Watchful Waiting for Men With Clinically Localized Prostate Cancer," Journal of the National Cancer Institute Monographs, vol. 45, Dec. 2012, 7 pp.
Langer et al., "Prostate Cancer Detection With Multi-parametric MRI: Logistic Regression Analysis of Quantitative T2, Diffusion-Weighted Imaging, and Dynamic Contrast-Enhanced MRI," Journal of Magnetic Resonance Imaging, vol. 30, No. 2, Aug. 2009, 8 pp.
Anderson et al., "Multiparametric MRI identifies and stratifies prostate cancer lesions: Implications for targeting intraprostatic targets," Brachytherapy, vol. 13, No. 3, May-Jun. 2014, 9 pp.
Barentsz et al., "ESUR prostate MR guidelines 2012," Eur Radiol, Feb. 10, 2012, 12 pp.
Chan et al., "Detection of prostate cancer by integration of line-scan diffusion, T2-mapping and T2-weighted magnetic resonance imaging; a multichannel statistical classifier," Med. Phys., vol. 30, No. 9, Sep. 2003, 10 pp.
Chappelow et al., "Elastic registration of multimodal prostate MRI and histology via multiattribute combined mutual information," Med. Phys., vol. 38, No. 4, Apr. 2011, 15 pp.
Delongchamps et al., "Multiparametric magnetic resonance imaging for the detection and localization of prostate cancer: combination of T2-weighted, dynamic contrast-enhanced and diffusion-weighted imaging," BJU International, vol. 107, No. 9, May 2011, 8 pp.
Dickinson et al., "Magnetic Resonance Imaging for the Detection, Localisation, and Characterisation of Prostate Cancer: Recommendations from a European Consensus Meeting," European Urology, vol. 59, Dec. 21, 2010, 18 pp.
Divrik et al., "Increasing the number of biopsies increases the concordance of Gleason scores of needle biopsies and prostatectomy specimens," Urologic Oncology: Seminars and Original Investigations, vol. 25, No. 5, Sep.-Oct. 2007, 7 pp.
Efron et al., "An Introduction to the Boostrap," CRC Press, 1998, 11 pp. (Applicant points out, in accordance with MPEP 609.04(a), that the year of publication, 1998, is sufficiently earlier than the effective U.S. filing date, Apr. 3, 2015, so that the particular month of publication is not in issue.).
Eichelberger et al., "Predicting Tumor Volume in radical Prostatectomy Specimens From Patients With Prostate Cancer," Am J Clin Pathol, vol. 120, No. 3, Sep. 2003, 6 pp.
Friedman et al., "Regularization Paths for Generalized Linear Models via Coordinate Descent," Journal of Statistical Software, vol. 33, No. 1, Jan. 2010, 22 pp.
Garcia-Reyes et al., "Detection of prostate cancer with multiparametric MRI (mpMRI): effect of dedicated reader education on accuracy and confidence of index and anterior cancer diagnosis," Abdom Imagine, vol. 41, No. 1, Jan. 2015, 20 pp.
Gibbs et al., "Comparison of Quantitative T2 Mapping and Diffusion-Weighted Imagine in the Normal and Pathologic Prostate," vol. 46, No. 6, Dec. 2001, 5 pp.
Hedgire et al., "Multiparametric magnetic resonance imaging of prostate cancer," Indian J Radiol Imaging, vol. 22, No. 3, Jul.-Sep. 2012, 24 pp.
Homer et al., "Driven-Equilibrium Single-Pulse Observation of T1 Relaxation/ A Reevaluation of a Rapid "New," Method for Determining NMR Spin-Lattice Relaxation Times," Journal of Magnetic Resonance, vol. 63, No. 2, Jun. 15, 1985, 11 pp.
Kalavagunta et al., "Analysis of Quantitative MRI and Pathology based on Co-registered Regions of Prostate Cancer," Proc. Intl. Soc. Mag. Reson. Med., vol. 20, 2012, 1 pp. (Applicant points out, in accordance with MPEP 609.04(a), that the year of publication, 2012, is sufficiently earlier than the effective U.S. filing, Apr. 3, 2015, so that the particular month of publication is not in issue.).
Kalavagunta et al., "Registration of In Vivo Prostate MRI and Pseudo-Whole Mount Histology Using Local Affine Transformations Guided by Internal Structures (LATIS)," Journal of Magnetic Resonance Imaging, vol. 41, No. 4, Apr. 2015, 11 pp.

(56) References Cited

OTHER PUBLICATIONS

Kim et al., "Localization of Prostate Cancer Using 3T MRI, Comparison of T2-Weighted and Dynamic Contrast-Enhanced Imaging," J Comput Assist Tomogr, vol. 30, No. 1, Jan.-Feb. 2006, 5 pp.
Kurhanewicz et al., "Multiparametric magnetic resonance imaging in prostate cancer: present and future," Curr Opin Urol, vol. 18, No. 1, Jan. 2008, 7 pp.
Le Bihan et al., "Separation of Diffusion and Perfusion in Intravoxel Incoherent Motion MR Imaging," Radiology, vol. 168, No. 2, Aug. 1988, 9 pp.
Liney et al., "Comparison of Conventional Single Echo and Multi-Echo Sequences with a Fast Spin-Echo Sequence for Quantitative T2 Mapping: Application to the Prostate," JMRI, Jul. 1996, 5 pp.
Liney et al., "In Vivo Quantification of Citrate Concentration and Water T2 Relaxation Time of the Pathologic Prostate Gland using 1H MRS and MRI," Magnetic Resonance Imaging, vol. 15, No. 10, Jul. 20, 1997, 10 pp.
Litjens et al., "Computer-Aided Detection of Prostate Cancer in MRI," IEEE Transactions on Medical Imaging, vol. 33, No. 5, May 2014, 10 pp.
Matulewicz et al., "Anatomic segmentation improves prostate cancer detection with artificial neural networks analysis of 1H MRSI," J Magn Reson Imaging, vol. 40, No. 6, Dec. 2014, 18 pp.
Morton et al., "Screening Mammograms: Interpretation with Computer-aided Detection—Prospective Evaluation," Radiology, vol. 239, No. 2, May 2006, 9 pp.
Mullerad et al., "Prostate Cancer: Detection of Extracapsular Extension by Genitourinary and General Body Radiologists at MR Imaging," vol. 232, No. 1, Jul. 2004, 7 pp.
Niaf et al., "Computer-aided diagnosis of prostate cancer in the peripheral zone using multiparametric MRI," Physics in Medicine and Biology, vol. 57, No. 23, Jun. 21, 2012, 20 pp.
Orczyk et al., "Imaging of prostate cancer: a platform for 3D co-registration of in-vivo MRI ex-vivo MRI and pathology," Proc SPIE, Feb. 23, 2012, 18 pp.
Pakrer et al., "Experimentally-Derived Functional Form for a Population-Averaged High-Temporal-Resolution Arterial Input Function for Dynamic Contrast-Enhanced MRI," Magnetic Resonance in Medicine, vol. 56, No. 5, Nov. 2006, 8 pp.
Puech et al., "Computer-assisted diagnosis of prostate cancer using DCE-MRI data: design, implementation and preliminary results," Int J CARS, vol. 4, Oct. 21, 2008, 10 pp.
Rosenkrantz et al., "Prostate Cancer Localization Using Multiparametric MR Imagine: Comparison of Prostate Imaging Reporting and Data System (PI-RADS) and Likert Scales," Radiology, vol. 269, No. 2, Nov. 2013, 11 pp.
Ruprecht et al., "MRI of the prostate: Interobserver agreement compared with histopathologic outcome after radical prostatectomy," European Journal of Radiology, vol. 81, Dec. 28, 2010, 5 pp.
Sanda et al., "Quality of Life and Satisfaction with Outcome among Prostate-Cancer Survivors," The New England Journal of Medicine, vol. 358, No. 12, Mar. 20, 2008, 12 pp.
Shah et al., "Decision support system for localizing prostate cancer based on multiparametric magnetic resonance imaging," Med. Phys., vol. 39, No. 7, Jul. 2012, 11 pp.
Stember et al., "Pilot Study of a Novel Tool for Input-Free Automated Identification of Transition Zone Prostate Tumors using T2- and Diffusion-Weighted Signal and Textural Features," Journal of Magnetic Resonance Imaging, vol. 40, No. 2, Aug. 2014, 5 pp.
Thoeny et al., "Diffusion-Weighted Imaging of the Parotid Gland: Influence of the Choice of b-Values on the Apparent Diffusion Coefficient Value," Journal of Magnetic Resonance Imaging, vol. 20, No. 5, Nov. 2004, 5 pp.
Tiwari et al., "Multimodal Wavelet Embedding Representation for data Combination (MaWERiC): Integrating Magnetic Resonance Imaging and Spectroscopy for Prostate Cancer Detection," NMR Biomed, vol. 25, No. 4, Apr. 2012, 30 pp.
Tofts et al., "Modeling Tracer Kinetics in Dynamic Gd-DTPA MR Imaging," JMRI, vol. 7, No. 1, Jan.-Feb. 1997, 11 pp.
Viswanath et al., "Central Gland and Peripheral Zone Prostate Tumors Have Significantly Different Quantitative Imaging Signatures on 3 Tesla Endorectal, In Vivo T2-Weighted MR Imagery," Journal of Magnetic Resonance Imaging, vol. 36, No. 1, Jul. 2012, 12 pp.
Vos et al., "Automatic computer-aided detection of prostate cancer based on multiparametric magnetic resonance image analysis," Physics in Medicine and Biology, vol. 57, Mar. 6, 2012, 17 pp.
Vos et al., "Computer-assisted analysis of peripheral zone prostate lesions using T2-weighted and dynamic contrast enhanced T1-weighted MRI," Physics in Medicine and Biology, vol. 55, Mar. 2, 2010, 17 pp.
Kalavagunta et al., "Registration of In-vivo Prostate MRI and Pseudo Whole Mount Histology using Local Affine Transformation with Internal Structures (LATIS)," Journal of Magnetic Resonance Imaging, Wiley Periodicals, Inc., Apr. 4, 2014, 11 pp.
Wei et al., "Comprehensive Comparison of Health-Related Quality of Life After Contemporary Therapies for Localized Prostate Cancer," Journal of Clinical Oncology, vol. 20, No. 2, Jan. 15, 2002, 10 pp.

* cited by examiner

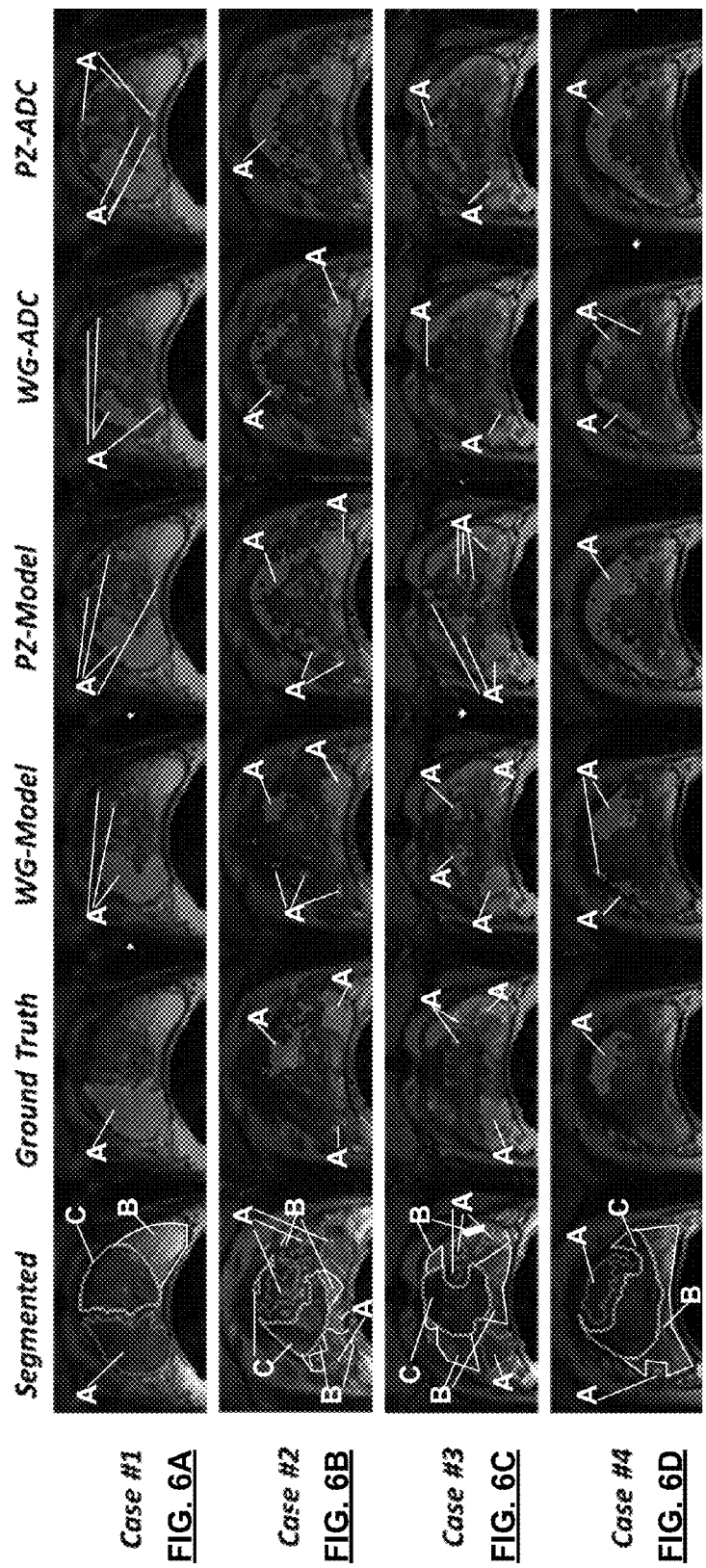

Case #1

Case #2

Case #3

Case #4

MEDICAL IMAGING DEVICE RENDERING PREDICTIVE PROSTATE CANCER VISUALIZATIONS USING QUANTITATIVE MULTIPARAMETRIC MRI MODELS

This application claims the benefit of U.S. Provisional Patent Application No. 62/142,815, filed Apr. 3, 2015, the entire contents of which are incorporated herein by reference.

STATEMENT REGARDING FEDERALLY SPONSORED RESEARCH OR DEVELOPMENT

This invention was made with government support under CA131013 awarded by the National Institutes of Health. The government has certain rights in the invention.

BACKGROUND

Current diagnostic tests, including digital rectal exams (DRE), serum prostate specific antigen (PSA) and transrectal ultrasound (TRUS) guided biopsy, do not provide the information needed to confidently diagnose and manage prostate cancer (PCa) in an optimized, cost effective way. Serum PSA has low specificity, and random TRUS guided biopsy can result in underestimation of the presence, extent and grade of PCa. Uncertainty regarding the accurate assessment of grade and disease extent, particularly for men with apparent low-risk disease has limited the adoption of active surveillance despite the fact that it is considered by many to be the preferred initial management strategy for these men. This limitation has contributed to the significant overtreatment of prostate cancer with high costs to the healthcare system, and increased morbidity resulting in lower quality of life for many men.

SUMMARY

In general, the present disclosure describes medical imaging analysis systems configured to render predictive prostate cancer visualizations using quantitative multiparametric magnetic resonance imaging (mpMRI) models developed using co-registered correlative histopathology. The disclosure provides techniques for developing and using mpMRI models for user-independent, voxel-wise detection and visualization of prostate cancer (PCa) utilizing co-registered correlative histopathology as the ground truth.

In one example, a medical imaging analysis device comprises a computer-readable storage medium storing a first parametric map that maps imaged tissue of a patient using values of a first parameter, and a second parametric map that maps the imaged tissue using values of a second parameter, wherein the first parametric map and the second parametric map are generated from medical imaging data for the imaged tissue. A processor coupled to the computer-readable storage medium is configured to apply a multiparametric model to the first parametric map and the second parametric map to generate at least one Composite Biomarker Score (CBS) for the imaged tissue of the patient. The multiparametric model specifies a multiparametric operation based on at least the first parameter and the second parameter that is based on co-registered histopathology data and respective sets of medical imaging training data. In one example, the multiparametric model specifies a multiparametric operation based on at least the first parameter and the second parameter that is based on models developed from separate data consisting of co-registered histopathology data and respective sets of medical imaging training data. The processor is further configured to generate and output, based on the respective CBS for each voxel of the imaged tissue, a visual indication of whether the corresponding imaged tissue is predicted to include cancer. The indication may, for example, comprise an overlay image for the medical imaging data for the imaged tissue, the overlay including regions of the predicted cancer.

In another example, a method comprises receiving, by a computing device, a first parametric map that maps imaged tissue of a patient using values of a first parameter, and a second parametric map that maps the imaged tissue using values of a second parameter, wherein the first parametric map and the second parametric map are generated from medical imaging data for the imaged tissue. The method further comprises applying, by the computing device, a multiparametric model to the first parametric map and the second parametric map to generate a respective Composite Biomarker Score (CBS) for each voxel of the imaged tissue, wherein the multiparametric model specifies a multiparametric operation based on at least the first parameter and the second parameter that is based on co-registered histopathology data and respective sets of medical imaging training data. In addition, the method comprises generating, by the computing device and based on the respective CBS for each voxel of the imaged tissue, a visual indication of whether the corresponding imaged tissue is predicted to include cancer; and outputting, by the computing device, the indication.

In another example, a method includes receiving, by a computing device, respective sets of training data corresponding to imaged tissue of a plurality of patients, wherein each respective set of training data comprises a first parametric map that maps imaged tissue of a respective patient using values of a first parameter, and a second parametric map that maps the imaged tissue using values of a second parameter, and wherein the first parametric map and the second parametric map are generated based on a respective set of medical imaging data for the imaged tissue. The method further includes receiving, by the computing device, respective digitized, annotated histopathology specimens that indicate the existence of cancer regions in the imaged tissue; co-registering, by the computing device, the respective sets of training data with the respective histopathology specimens; and determining, by the computing device and based on the co-registered respective sets of training data and respective histopathology specimens, a model for cancer prediction, wherein the model comprises a multiparametric operation based on at least the first parameter and the second parameter.

As such, techniques are described for generating a model used to provide predicted PCa visualizations, in which patients electing surgery are imaged preoperatively with an mpMRI protocol. Post-surgical prostatectomy specimens are processed using a study specific protocol providing digitally annotated histology slides which are volumetrically reassembled. Areas of pathologically identified cancer from cancer lesions contributed by patients are deformably mapped from histopathology to in-vivo MM. Voxels from mapped cancer and non-cancer are used to develop and evaluate individual quantitative MM (qMR) parameters for PCa detection. Predictive models which provide composite biomarker scores (CBS) are determined from multiple combinations of qMR parameters. Model development and evaluations of individual qMR and CBS may be performed separately for the peripheral zone (PZ) alone and the whole gland (WG=PZ+central gland). Based on developed models, visualizations may be generated that display predicted PCa.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 6A-6D are a set of images showing output four example cases.

DETAILED DESCRIPTION

Multiparametric magnetic resonance imaging (mpMRI) continues to evolve as an increasingly valuable tool in the diagnosis and management of prostate cancer (PCa). Even with the recognized potential of mpMRI demonstrated in the literature, the detection of PCa in clinical practice remains challenging as diagnostic performance is highly dependent on reader experience and expertise. Experienced radiologists with specific prostate imaging experience have been shown to demonstrate significantly higher accuracy and improved performance when compared to experienced radiologists without subspecialty advanced knowledge in prostate MRI. This variability in performance persists even with the development and utilization of early standards for the interpretation and reporting of mpMRI prostate data such as PI-RADS. As these standards continue to be developed and are adopted clinically, important questions still remain regarding how best to combine the relative importance of each acquisition composing the mpMRI exam. Additionally, there is a need to improve and standardize diagnostic performance in a way that is independent of interpreter skill and experience. The development of quantitative models for reliably and objectively interpreting mpMRI data may represent an ideal solution.

Predictive models, which can be trained to identify disease from the mpMRI data, are an alternative or adjunct to direct radiologic interpretation. Constructing such models requires the use of correlative histopathology. Both biopsy and post prostatectomy histopathology have been used as ground truths for model development and testing. One method is to use post-surgical prostatectomy specimens because the cancer location, extent and grade are available for both the development and testing of these models.

The techniques of the present disclosure develop and evaluate mpMRI models for the user-independent, voxel-wise detection of prostate cancer (PCa) utilizing co-registered correlative histopathology as the ground truth. The approach described herein removes the manual mapping of cancer and non-cancer regions from histopathology to MRI as well as the need for whole mount pathology sections. Using these methods, predictive models may be constructed and used to generate and render visualizations that differentiate cancer from non-cancer in both the peripheral zone and over the whole prostate.

Figure 1:
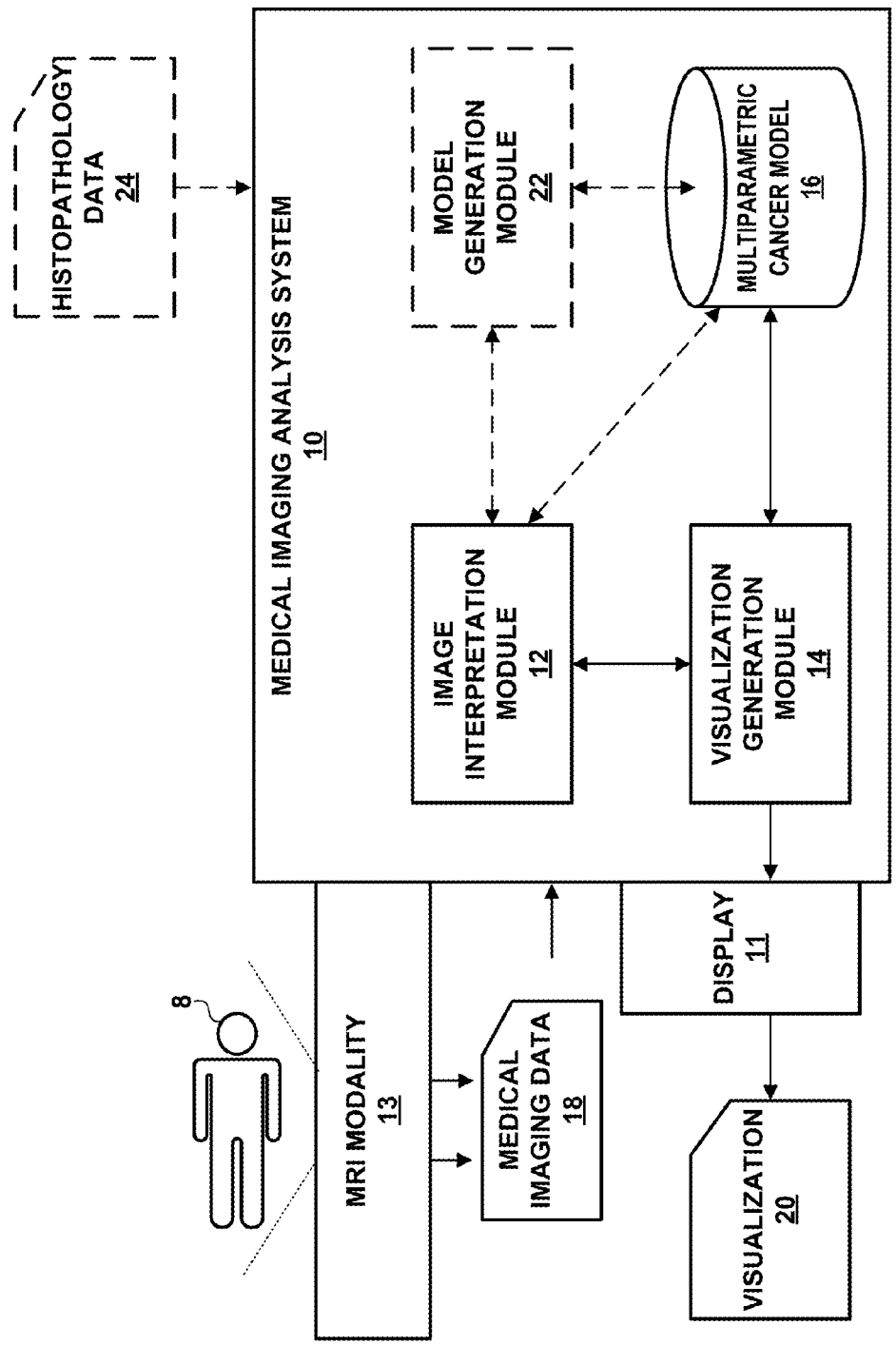
FIG. 1 is a block diagram illustrating an example medical imaging analysis system configured in accordance with one or more techniques of the present disclosure.

FIG. 1 is a block diagram illustrating an example medical imaging analysis system 10 ("system 10") in accordance with one or more techniques of the present disclosure. In the example of FIG. 1, system 10 may represent a computing device or computing system, such as a mobile computing device (e.g., a smartphone, a tablet computer, a personal digital assistant, and the like), a desktop computing device, a server system, a distributed computing system (e.g., a "cloud" computing system), or any other device capable of receiving medical imaging data 18 and performing the techniques described herein. In other examples, system 10 may be a medical imaging device, such as a magnetic resonance imaging (Mill) system, having a Multiparametric magnetic resonance imaging (mpMRI) input modality 13 for producing medical imaging data 18 and/or receiving the medical imaging data from other devices. As described herein, system 10 automatically constructs multiparametric medical imaging models and/or computationally applies such models to generate predictive prostate cancer visualizations for use in medical diagnosis, medical research, medical testing, or other fields. In accordance with the techniques described herein, system 10 may receive as input, medical imaging data, such as medical imaging data 18, and provide one or more visualizations (e.g., results 20) that indicate predicted cancer.

As shown in the example of FIG. 1, system 10 includes image interpretation module 12, visualization generation module 14, and multiparametric cancer model 16. In some examples, system 10 may also include database model generation module 22. Each of modules 12, 14, and 22 may be hardware, firmware, software, or some combination thereof. When implemented in software, modules 12, 14, and 22 comprises software instructions that execute on one or more programmable processors of system 10. Model 16 may, in the example of FIG. 1, represent a data repository or other collection of information that is accessible and/or modifiable by one or more of modules 12, 14, and 22 and stored on a computer-readable storage medium (e.g., disk or memory) of system 10.

Image interpretation module 12, in the example of FIG. 1, is configured to receive and process medical imaging data 18. Medical imaging data 18, in various examples, may be data that represents one or more images of tissue of patient 8. That is, medical imaging data 18 may be generated by a medical imaging device, such as a magnetic resonance imaging (MM) machine, when the medical imaging device scans tissue of patient 8. As one example, medical imaging data 18 may represent various two-dimensional (2D) images of a prostate gland of patient 8.

Each 2D image may be a different plane of the scanned tissue. That is, the medical imaging device that generates medical imaging data 18 may take multiple 2D scans, each at a different point along a third dimension. In this way, the composite of medical imaging data 18 may, in some examples, be a series of planes (e.g., "sections") of the scanned tissue.

Image interpretation module 12 receives medical imaging data 18 and determines one or more 2D parameter maps corresponding to the imaged tissue. A 2D parameter map may indicate the value of a parameter at each location of the scanned tissue. For instance, image interpretation module 12 may generate a parameter map for one or more of an apparent T2 (T2) parameter, an apparent diffusion coefficient (ADC) parameter, pharmacokinetic parameters $K^{Trans}$, $k_{ep}$, and/or an area under the gadolinium concentration time curve over 90 s (AUGC90) parameter. In other words, image interpretation module 12 may process medical imaging data 18 to determine multiparametric mappings of the imaged tissue. Image interpretation module 12 may send the parameter mappings to one or more other components of analysis system 10, such as to visualization generation module 14.

In the example of FIG. 1, visualization generation module 14 is operable to analyze parameter maps received from image interpretation module 12 by applying one or more multiparametric cancer models 16. Based on the analysis of the parameter maps, visualization generation module 14 generates information indicating whether the imaged tissue has predicted cancer. That is, visualization generation module 14 applies multiparametric cancer model 16 to predict, based on medical imaging data 18, whether various regions of the tissue of patient 8 includes cancerous tissue and, based on the analysis, produce a graphical visualization illustrating the prediction. As one example, visualization generation module 14 may create an overlay image for medical imaging data 18 that shows and identifies regions of the imaged tissue that are predicted to be cancer. The overlay may, in some examples, visually depict areas of the tissue (as shown in medical imaging data 18) that are predicted to be cancer based on multiparametric cancer model 16.

Visualization generation module 14, in the example of FIG. 1, generates and outputs for display visualization 20, including at least an indication of the predicted cancer. Visualization 20 may, in some examples, be a 2D or 3D graphical representation of the imaged tissue, with visual indications of cancer regions (e.g., cancer lesions). In some examples, visualization 20 may be output for display, such as at a display device 11 operatively coupled to analysis system 10. In other examples, visualization 20 may be output to one or more other devices for further processing, storage, and/or display.

In some examples, system 10 may include model generation module 22. Model generation module 22 of system 10 may use medical imaging training data (e.g., received from imaged interpretation module 12) and corresponding histopathology data 24 to generate multiparametric cancer module 16. That is, model generation module 22 may receive medical imaging training data from image interpretation module 12 and may receive histopathology data 24. Histopathology data 24 may be annotated, digitized images of the tissue(s) shown in the received medical imaging training data. For instance, histopathology data 24 may be created by excising or removing the imaged tissue, fixing the tissue, and sectioning the tissue. The sectioned tissue may be digitized and annotated to indicate regions of the tissue that actually are cancer. Model generation module 22 may use the digitized and annotated histopathology data to determine characteristics of medical imaging data that corresponds to actual cancer. In order to do so, model generation module 22 may register the histopathology data to the medical imaging training data so that a specific location in a digitized image from histopathology data 24 corresponds (at least substantially) to the same actual location as the specific location in an image of the medical imaging training data. That is, model generation module may modify or otherwise adjust histopathology data 24 to "fit" the corresponding medical imaging training data. Methods for registering the histopathology data are further described herein.

Using the registered histopathology data 24 and medical imaging training data, model generation module 22 may generate a predictive cancer model and store the model as multiparametric cancer model 16. In some examples, the model may represent an equation that, when applied to values of parameters in medical imaging data 18, results in a score (e.g., a Composite Biomarker Score or CBS) that indicates whether or not the corresponding tissue is likely to be cancer. For instance, model 16 may, in some examples, be a set of coefficients for respective parameters and/or threshold CBS values. For each value of the parameter maps for imaged tissue, the parameter values may be plugged into the equation, and the resulting CBS value may be evaluated against the threshold CBS values. If the threshold values are satisfied, analysis system 10 may indicate that the corresponding tissue is likely cancer.

In this way, analysis system 10 may be used to generate a multiparametric cancer model using medical imaging data and co-registered histopathology data, and/or use the multiparametric model to provide at least one indication of whether or not imaged tissue includes cancer.

Figure 2:
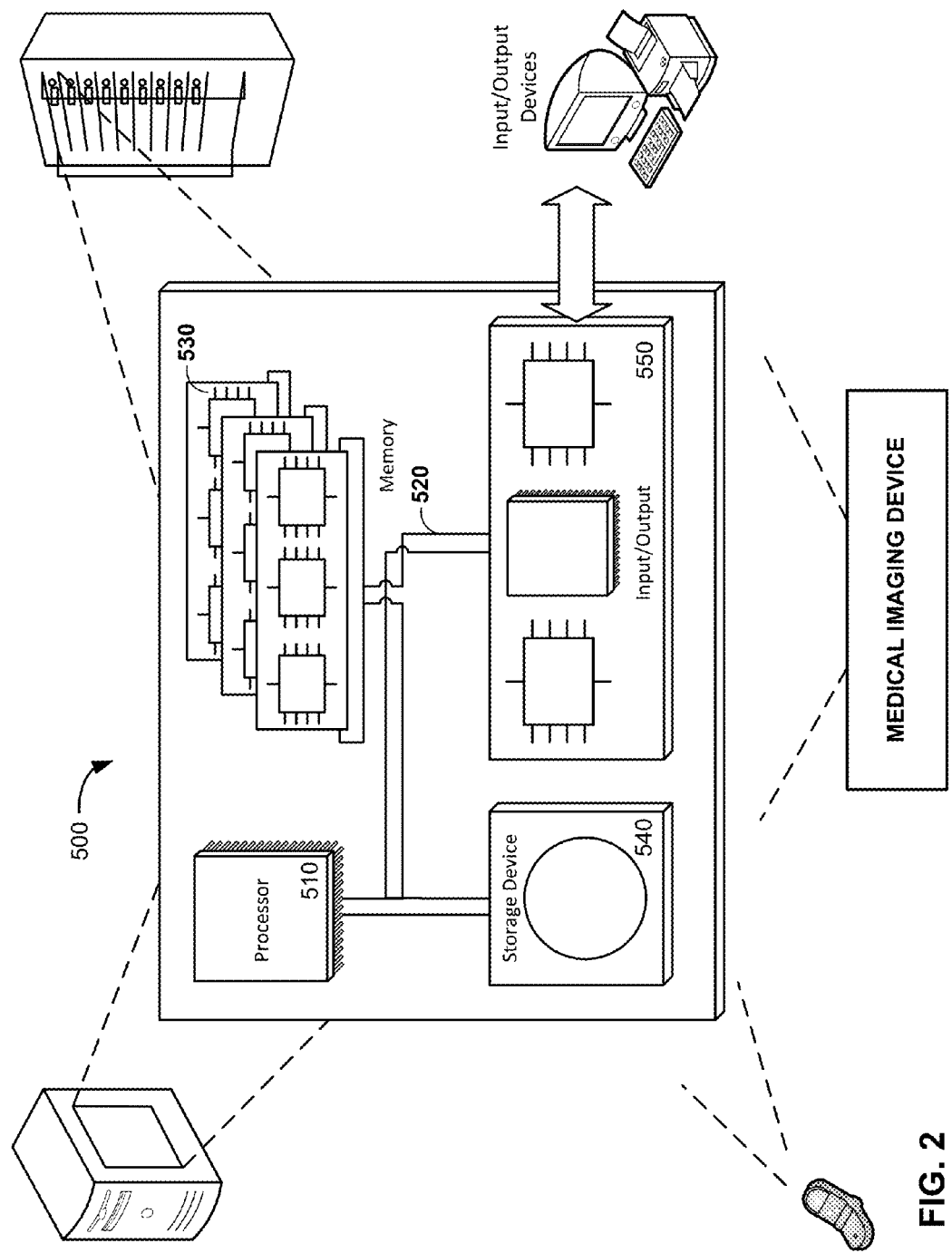
FIG. 2 is a block diagram illustrating an example of various devices that may be configured to implement one or more techniques of the present disclosure.

FIG. 2 is a block diagram illustrating a detailed example of various devices that may be configured to implement one or more techniques of the present disclosure. That is, device 500 of FIG. 2 provides an example implementation for the medical imaging analysis system 10 of FIG. 1. Device 500 may be a medical imaging device, such as a magnetic resonance imaging (MM) system, a mobile device (e.g., a tablet, a personal digital assistant, or other mobile device), a workstation, a computing center, a cluster of servers, or other examples of a computing environment, centrally located or distributed, that is capable of executing the techniques described herein. Any or all of the devices may, for example, implement portions of the techniques described herein for generating and outputting predicted prostate cancer visualizations for display.

In the example of FIG. 2, computer-implemented device 500 includes a processor 510 that is operable to execute program instructions or software, causing the computer to perform various methods or tasks, such as performing the techniques for generating and/or using multiparametric models for prostate cancer prediction as described herein. Processor 510 is coupled via bus 520 to a memory 530, which is used to store information such as program instructions and/or other data while the computer is in operation. A storage device 540, such as a hard disk drive, nonvolatile memory, or other non-transient storage device stores information such as program instructions, data files of the multidimensional data and the reduced data set, and other information. The computer also includes various input-output elements 550, including parallel or serial ports, USB, Firewire or IEEE 1394, Ethernet, and other such ports to connect the computer to external devices such a printer, video camera, display device, medical imaging device, surveillance equipment or the like. Other input-output elements include wireless communication interfaces such as Bluetooth, Wi-Fi, and cellular data networks.

The computer itself may be a traditional personal computer, a rack-mount or business computer or server, or any other type of computerized system. The computer, in a further example, may include fewer than all elements listed above, such as a thin client or mobile device having only some of the shown elements. In another example, the computer is distributed among multiple computer systems, such as a distributed server that has many computers working together to provide various functions.

As one example of experimental results for model creation, between November 2009 and August 2012, patients with biopsy-proven prostate cancer were recruited to participate in an MM study utilizing an endorectal coil (ERC). Informed consent was obtained under an institutional review board approved protocol. Inclusion of patient data in the final analysis set required 1) a complete mpMRI dataset free from significant motion artifacts 2) whole-organ tissue procured from definitive surgery, free from sectioning artifacts, 3) lesion volumes $\geq 0.2$ cm$^3$ and 4) reasonable anatomic correspondence between assembled post-surgical histopathology and in vivo MRI data based on visual inspection, following study specific protocols described in the section on correlative histopathology.

Multiparametric 3T MM data was acquired using a clinical 3 Tesla scanner (Tim TRIO; Siemens Medical Solutions, Erlangen, Germany). A surface array coil combined with an inflatable ERC (Medrad, N.J., USA) was used for signal reception. Perfluorocarbon (Fluorinert; 3M, Saint Paul, Minn.) was used for coil inflation to minimize susceptibility mismatches. An 18 French (6.0 mm) urethral catheter (Robinson Model, C.R. Bard Inc. Murray Hill, N.J.) was inserted into the rectum parallel and posterior to the ERC to deflate gases proximal to the coil. No antiperistalsis drugs were used in the course of these studies.

After confirming adequate positioning of the ERC on scout images, the rest of each MM study included the following acquisitions, which are further detailed in Table 1:
1. Anatomic imaging using a $T_2$-weighted ($T_2$w) Turbo Spin Echo ($T_2$-TSE) sequence in the axial, sagittal and coronal planes.
2. Additional TSE datasets acquired in the axial plane at different echo times for calculating $T_2$ maps ($T_2$-TSE).
3. $T_1$-weighted Turbo Spin Echo ($T_1$-TSE) imaging for the detection of post-biopsy hemorrhage.
4. Single Shot Echo Planar Imaging (EPI) diffusion weighted imaging (DWI) for calculation of Apparent Diffusion Coefficient (ADC) maps.
5. 3D gradient echo data sets for calculating $T_1$ maps using DESPOT1 (Driven Equilibrium Single Pulse Observation of $T_1$).
6. Dynamic Contrast Enhanced MM (DCE-MM) using 3D Flash VIBE (Volume Interpolated Breath-hold Examination ($T_1$w 3D-GRE).

All studies were run in the first-level control mode with prostate specific power and Bo adjustment. When specific absorption rates (SAR) limits were exceeded with TSE imaging, longer repetition times (TRs) were used. For DCE-MRI, the maximum flip angle was adjusted downward to reduce power deposition as guided by system derived SAR limits.

TABLE 1

MRI Acquisition Parameters

| | TSE $T_2$w Anatomic | TSE T2 mapping | TSE $T_1$w | DWI | DESPOT T1 mapping | DCE |
|---|---|---|---|---|---|---|
| Sequence | TSE | TSE | TSE | SSH-EPI | GRE | GRE |
| Scan Duration (mm:ss) | 4:56 | 2:28 | 1:15 | 4:27 | 0:25 | 4:59 |
| TR(ms) | ≥6000 | ≥6000 | 500 | 3200 | 4.09 | 4.09 |
| TE(ms) | 107 | 30, 72, 144 | 13 | 88 | 1.44 | 1.44 |
| Slice Thickness (mm) | 3 | 3 | 3 | 3 | 4 | 4 |
| Acquisition Matrix | 256 × 230 | 256 × 230 | 256 × 192 | 128 × 128 | 192 × 163 | 192 × 163 |
| Slices | 19 | 19 | 19 | 19 | 19 | 19 |
| FOV (mm) | 140 | 140 | 160 | 180 | 220 | 220 |
| Oversampling (%) - Phase, (Slice) | 100 | 100 | 100 | 0 | 50, (38) | 50, (38) |
| Flip Angle (°) | 140† | 140† | 120† | 90 | 2, 5, 10, 15 | ≤10 |
| Echo Train Length | 23 | 23 | 3 | 95 | 1 | 1 |
| Readout Bandwidth (Hz/pixel) | 190 | 100 | 130 | 1395 | 401 | 401 |
| Number of averages | 2 | 2 | 1 | 8 | 4 | 1 |
| Number of phase encoding | 483 | 507 | 382 | 95 | 183 | 183 |

TABLE 1-continued

MRI Acquisition Parameters

| | TSE T$_2$w Anatomic | TSE T2 mapping | TSE T$_1$w | DWI | DESPOT T1 mapping | DCE |
|---|---|---|---|---|---|---|
| steps | | | | | | |
| Parallel Imaging R Factor | 1 | 2 | 2 | 2 | 2 | 2 |
| Nominal Voxel Size | 0.61 × 0.55 | 0.61 × 0.55 | 0.83 × 0.63 | 1.41 × 1.41 | 1.35 × 1.45 | 1.35 × 1.45 |
| Phase Encode Direction | LR | LR | LR | AP | LR | LR |
| Temporal resolution (s) | n.a | n.a | n.a | n.a | n.a | 6 |
| b-values (s/mm2) | n.a | n.a | n.a | 50, 400 800 | n.a | n.a |

T$_2$w T2 weighted
DCE Dynamic Contrast Enhanced
T$_1$w T1 weighted
TSE Turbo Spin Echo
SE Spin Echo Multi Echo
DESPOT Driven Equilibrium Single Pulse Observation of T$_1$
EPI Echo Planar Imaging
GRE Gradient Recalled Echo The acquired data allowed for the calculation of quantitative maps including apparent T2 (T2), apparent diffusion coefficient (ADC), and pharmacokinetic parameters K$^{Trans}$, k$_{ep}$ and area under the gadolinium concentration time curve over 90 s (AUGC90). This set of parameters will be collectively referred to herein as the quantitative MRI (qMR) data. Maps of prostate T2 values were calculated from the multiple TSE data sets using previously described and validated methods. T1 maps were generated using the 3D driven equilibrium single pulse observation of T$_1$ (DESPOT1) method. ADC maps were generated using the manufacturer's standard reconstruction from the single shot EPI acquisitions with 3 b-values (50, 400, 800 s/mm$^2$) and multi-directional encoding (manufacturer's "3-scan trace"). A b-value of 0 s/mm$^2$ was avoided to reduce the confounding effects of perfusion on ADC calculations. The DCE-MRI acquisition consisted of 50 dynamic volumes acquired with 6 s temporal resolution for a total acquisition time of 5 min. Three volumes were acquired before the injection of 0.1 mM/kg of gadopentetate dimeglumine (Magnevist; Bayer Schering AG, Berlin, Germany) at a rate of 3 ml/s followed by a 30 ml saline flush at the same rate. Pharmacokinetic maps were generated by using a modified Tofts model with a previously published population averaged arterial input function (AIF). The fitted model provided the following pharmacokinetic parameters: K$^{trans}$ (Forward Volume Transfer Constant, min−1), k$_{ep}$ (Reflux Rate between the Extracellular Space and the Plasma, min$^{-1}$), v$_e$ (Fractional Extravascular Extracellular Space, v$_e$=K$^{trans}$/k$_{ep}$) and AUGC90. An r$^2$ goodness-of-fit ≥0.85 was required in order for the pharmacokinetic model parameters to be included in subsequent single or multi parameter analysis. The T2 mapping, T1 mapping and pharmacokinetic modeling software was programmed in IDL (ITT Boulder, Colo.).

Resected prostates were sectioned, and resulting slides were digitized and annotated (i.e. marking of cancer extent) by following a previously-published protocol developed to improve the correspondence between the pathology sectioning and in vivo MM slice planes. In summary, the resected prostates were positioned in a sectioning box with the posterior edge parallel to the bottom and perpendicular to cutting guides. Co-planar axial sections 3 mm thick were initially cut, and then further sub-sectioned into quarters or halves so that the subsequent 4 μm hematoxylin and eosin (H&E) stained sections made from the tissue blocks could fit on standard slides for digitization and storage.

FIGS. 3A-3D are a set of images showing (a) digitized and annotated pathology specimens assembled into a pseudo-whole mount (PWM) from 4 quarter-mount slides; (b) an annotated region of cancer from histopathology, deformably registered to the corresponding anatomic T$_2$w image using LATIS; (c) how the prostate pseudo-capsule and central gland were identified on the anatomic T2w images (dashed curve 32) to provide zonal information; and (d) a volumetrically reassembled prostate that allows grouping of annotations for lesion identification and volume determination.

Figure 3D:
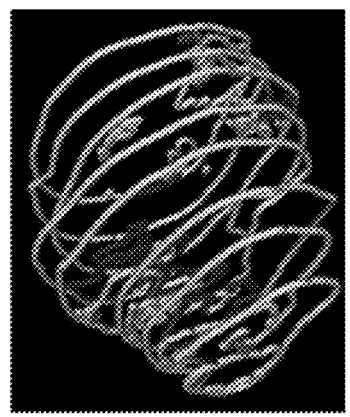
FIGS. 3A-3D are images showing (a) digitized and annotated pathology specimens assembled into a pseudo-whole mount (PWM) from 4 quarter-mount slides; (b) an annotated region of cancer from histopathology, deformably registered to the corresponding anatomic $T_2w$ image using LATIS; (c) how the prostate pseudo-capsule and central gland were identified on the anatomic T2w images (dashed curve) to provide zonal information; and (d) a volumetrically reassembled prostate that allows grouping of annotations for lesion identification and volume determination.
Figure 3C:
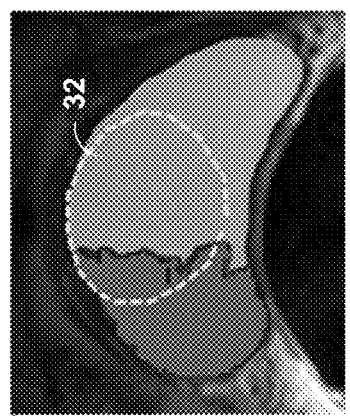
Figure 3B:
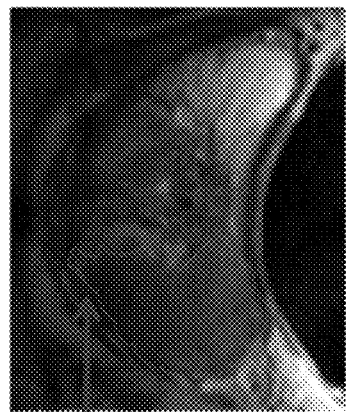
Figure 3A:
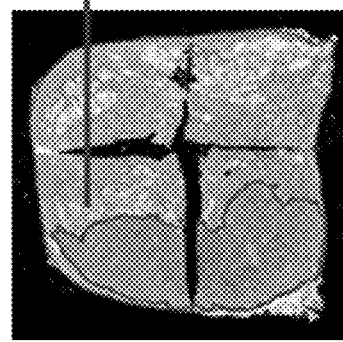
Figure 4C:
FIGS. 4A-4F are images showing examples of parametric maps used in the mpMRI analysis, with (a) being the reference anatomic T2w TSE image, followed by the corresponding maps of (b) ADC, (c) T2, (d) $K^{Trans}$, (e) $k_{ep}$ and (f) AUGC90.
Figure 4B:
Figure 4A:
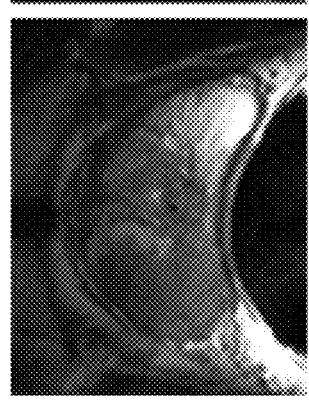
Figure 4F:
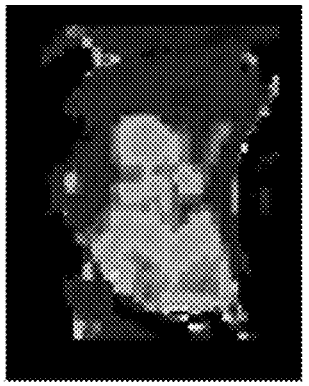
Figure 4E:
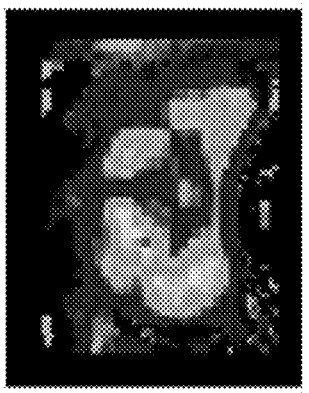
Figure 4D:
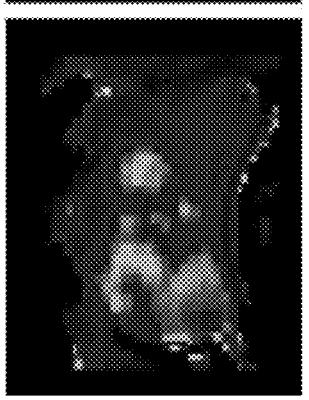

Specifically, the digitized and annotated histopathology specimens were then assembled into pseudo-whole mount (PWM) slices as shown in FIG. 3A and volumetrically reassembled as shown in FIG. 3D. This volumetric reassembly allows continuous volumes of cancer to be linked together and defined as lesions. Lesion size in cubic centimeters may be calculated from the annotated regions using an assumed shrinkage factor of 25%.

The MM slice location corresponding to the center of each cancer lesion defined on histopathology may be determined by verifying the approximate distance from the apex, and existence of similar anatomic features between histopathology and the T2w anatomic images. Annotated regions of cancer from histopathology may then be registered to the corresponding anatomic T$_2$w image using the Local Affine Transformations guided by Internal Structures (LATIS) software package previously demonstrated to have a registration accuracy of 1.54±0.64 mm (FIG. 3B). To provide zonal information, the prostate pseudo-capsule, central gland (CG), and peripheral zone (PZ) may be identified on the anatomic T2w images using a semi-automated segmentation program (Segasist, Ontario, Canada), as shown in FIG. 3C.

The annotations from histology and MRI may be combined to define the following regions: non-cancer PZ (NC$_{PZ}$), non-cancer CG (NC$_{CG}$), cancer PZ (PC$_{PZ}$) and cancer CG (PC$_{CG}$). To generate the non-cancer regions, all registered cancer masks may be first subtracted from the prostate's pseudo-capsule mask determined from the anatomic $T_2w$ data. The cancer masks may then be dilated by 3 pixels (~1.5 mm) before subtraction to minimize the impact of registration errors. The $NC_{CG}$ may be given by the intersection of the segmented CG region and of the prostate pseudo-capsule, minus the dilated regions of cancer. The $NC_{PZ}$ region may be the remainder of the voxels not involved by cancer or determined to be within the pseudo-capsule.

These regions may subsequently be transferred onto each of the qMR datasets. As reliable methods to register between the mpMRI datasets are not yet developed and adjustments for motion may be necessary, a rigid body registration may be assumed to align the regions mapped and identified on the $T_2w$ anatomic series to the other qMR data. The relative through-plane and in-plane translations between the anatomic T2w images and the other functional acquisitions may be manually determined in OsiriX (Pixmeo, Geneva, Switzerland). If necessary, internal features and the borders of the prostate may be used to perform manual adjustment on each qMR dataset.

Model generation module 22 may generate two data pools from the annotated qMR data: the peripheral zone model (PZ-Model), including only the PCpz and NCpz regions, and the whole gland model (WG-Model), including all four regions ($PC_{PZ}+PC_{CG}$ and $NC_{PZ}+NC_{CG}$).

For the two data pools, both single parameter and multiple parameter analyses may be performed. The data pools may be individually filtered to remove parameter values of zero (resulting primarily from failed parametric mapping of the DCE-MRI and T2 data). A value of zero for one parameter may not exclude other, non-zero, parameters for that voxel from the single parameter analysis, but, in some examples, only voxels with non-zero values for all parameters are included in the multivariate analysis. Single parameters may be summarized for cancer and non-cancer voxels using the median values. Confidence intervals for the median and corresponding p-values may be calculated by using the bootstrap method, as further described herein. Only those individual parameters which show a significant difference ($p \leq 0.05$) between cancer and non-cancer voxels may be included as candidates in the subsequent multiparametric MRI (mpMRI) model development. The classification accuracy of each individual parameter may be evaluated using the receiver operating characteristic (ROC) curve and summarized using the area under the ROC curve (AUC) values.

Multiparametric modeling may be completed by model generation module 22 to develop a multi-parametric classifier that, when applied by image interpretation module 12, combines multiple biomarkers through a operation (function), $f(qMR(1), qMR(2), \ldots, qMR(n))$, specified in the model to calculate a composite biomarker score (CBS) for each voxel that is used to predict the presence of prostate cancer within the corresponding tissue. In some examples, multiparametric modeling may be performed by logistic regression with the least absolute shrinkage and selection operator (LASSO) penalty implemented using, for example, a glmnet package. LASSO may enable the development of models with increasing numbers of qMR parameters. The classification accuracy of these "n" parameter models can be evaluated using the ROC curve estimated by leave-one-out cross-validation. Further details on the use of the LASSO and cross-validation procedure are described below. From the n-parameter multiparametric model developed using the LASSO, a CBS may be calculated for each voxel, using a linear combination of the multiple qMR parameters, such that $$CBS = \beta_0 + \beta_{qMR(1)} \cdot qMR(1) + \beta_{qMR(2)} \cdot qMR(2) + \ldots \\ \cdot \beta_{qMR(n)} \cdot qMR(n), \quad \text{Eq. 1.}$$

where $\beta_0$ and $\beta_{qMR}$ are the regression parameters estimated from LASSO. The classification accuracy for the CBS may be summarized using the AUC from the cross-validation adjusted ROC curve along with the sensitivity corresponding to 90% specificity (S90) and subsequently compared to the AUC for the individual parameters to evaluate the benefit of the multiparametric approach compared to the best performing single-parameter. Confidence intervals for each predictor and p-values between the single best qMR predictor and the mpMRI models may be calculated by the bootstrap method following the re-sampling procedure described below. To assess the impact of CBS at the subject level, within-subject AUC values may be calculated and compared for both CBS and the best single parameter.

Confidence intervals and p-values for the single parameter and multiparametric analyses may utilize a two-stage bootstrap procedure to properly account for the correlation between voxels from the same slice. Slices may be resampled, with replacement, followed by resampling of voxels (with replacement within each slice). In some examples, this may be repeated a number of times (e.g., 1000 times) to generate 1000 re-sampled data sets. This procedure may give estimates of the sampling distribution for the various univariate and multivariate statistics and to calculate confidence intervals and p-values.

In accordance with one or more of the techniques described herein, model generation module 22 may generate multiparametric predictive models, in some examples, using logistic regression with a LASSO penalty. The number of parameters in the model may be controlled by the LASSO tuning parameter, with smaller tuning parameter values corresponding to models with more parameters. For instance, models with 2 to 5 parameters may be developed. In each case, the presented model may correspond to the largest tuning parameter that results in a model for a given number of parameters which corresponds to the "smallest" model, as defined by the LASSO penalty, for the given number of parameters. Such a solution is reasonable because of the relatively small number of independent subjects. The given models may result in the maximum shrinkage of the regression parameters towards zero. To calculate the CV-adjusted ROC curve, a system configured in accordance with the techniques described herein may use an iterative procedure where all voxels from a subject are dropped, the LASSO is refitted using the remaining data and the CBS is computed for all voxels from the subject that was dropped for that iteration. These data can then be used to calculate the ROC curve, resulting in a CV-adjusted ROC curve that accounts for the bias due to overfitting.

While described in some examples as a linear function of various parameters, the mpMRI model 16 may, in various examples, be a mathematical function of two or more parameters. That is, the multiparametric model may be determined using any number of available methods for model generation based on the correlated histopathology data. For instance, the mpMRI model may be generated using machine learning methods or other methods.

The voxel-wise application of the mpMRI model by image interpretation module 12 may enable the construction of CBS maps. Predictive maps of cancer may subsequently be determined from CBS maps using model dependent (i.e. PZ-Model and WG-Model) thresholds providing 90% sensitivity (i.e. S90 threshold). Predictive maps from CBS can be compared against those generated using the best performing single parameter.

In one example of experimental results for model application, 77 patients were imaged under this protocol. An example of the parametric results obtained from these patients is shown in FIGS. 4A-4F. In particular, FIGS. 4A-4F are images showing examples of parametric maps used in the mpMRI analysis, with (a) being the reference anatomic T2w TSE image, followed by the corresponding maps of (b) ADC, (c) T2, (d) $K^{Trans}$, (e) $k_{ep}$ and (f) AUGC90. From the original 77 patients imaged, 53 chose surgery as treatment and 2 were excluded due to excessive motion or incomplete DCE-MRI. After excluding 8 additional cases with poor sectioning and 7 with cancer lesions <0.2 cm³, the final patient population included in the current analysis totaled 36. Demographics, serum PSA, time between MM and surgery and pathologic tumor stage are reported for the 34 subjects in Table 2. From these patients, a total of 41 lesions were included in the construction of the predictive models. The Gleason scores and volumes of the included lesions are reported in Table 3.

TABLE 2

Clinical-Pathologic Features In the Study Population

| Age (y) | |
|---|---|
| Mean | 64 |
| Median | 65 |
| Range | 51-77 |
| Serum PSA (ng/mL) | |
| Mean | 8.3 |
| Median | 7.7 |
| Range | 1.3-21.8 |
| Time between MRI and Surgery (d) | |
| Mean | 16 |
| Median | 12 |
| Range | 1-69 |
| Pathologic Tumor Stage | |
| T2a | 3 |
| T2b | 4 |
| T2c | 16 |
| T3a | 7 |
| T3b | 4 |

TABLE 3

Lesion Features*

| Pathologic Gleason Score (PZ, CG) | |
|---|---|
| 3 + 3 | (0, 4) |
| 3 + 4 | (9, 3) |
| 4 + 3 | (9, 1) |
| 4 + 4 | (7, 0) |
| 4 + 5 | (5, 0) |
| 5 + 4 | (1, 0) |
| 5 + 5 | (2, 0) |
| Lesion Volumes on Histopathology (cm³) | |
| Mean | 2.3 |
| Median | 1.14 |
| Range | 0.2-17.5 |

*Values reported on a per lesion basis. A total of 41 lesions from the 34 patients.

Results from the single parameter voxel-wise analyses are shown in Table 4. Presented are the number of non-zero voxels for each parameter, the median for cancer and non-cancer voxels, p-value for comparing the median between cancer and non-cancer voxels, and AUC for discriminating between cancer and non-cancer voxels. Significant differences between cancer and non-cancer voxels were observed for T2TSE, ADC, $K^{trans}$, $k_{ep}$ and AUGC90 for both the PZ and WG pools (p<0.001 in all cases). A significant difference was observed for $v_e$ in voxels from the PZ pool (p=0.032) but not the WG pool (p=0.434), and the difference in the PZ pool was not significant after a Bonferonni adjustment, which requires a p-value of 0.05/14=0.0036 to declare significance. Therefore, T2TSE, ADC, $K^{trans}$, $k_{ep}$ and AUGC90 were included in the subsequent multiparametric analysis. Finally, as ADC was the best single discriminator between cancer and non-cancer voxels for both the PZ and WG pools it served as the primary basis for comparison with the multiparametric results.

TABLE 4

Comparison of median parameter values between cancer and non-cancer voxels

| | | Non-Cancer (NC) Voxels | | | Prostate Cancer (PC) Voxels | | | p-value PCa vs. Non-PCa | AUC |
|---|---|---|---|---|---|---|---|---|---|
| Model | Parameter | N | Median | 95% CI | N | Median | 95% CI | | |
| Peripheral Zone (PZ) | T2TSE (MS) | 33871 | 128 | (120, 137) | 19359 | 96 | (92, 104) | <0.001 | 0.74 |
| | TIDESPOT (ms) | 33871 | 1991 | (1851, 2204) | 19357 | 1921 | (1735, 2245) | 0.540 | 0.543 |
| | ADC × 10⁻⁶ (mm²/s) | 33796 | 1375 | (1324, 1433) | 19281 | 857 | (758, 973) | <0.001 | 0.825 |
| | $K^{Trans}$ × 10⁻³ (min⁻¹) | 32034 | 93 | (79, 108) | 18704 | 154 | (130, 186) | <0.001 | 0.734 |
| | $k_{ep}$ × 10⁻³ (min⁻¹) | 31169 | 422 | (367, 477) | 18491 | 586 | (504, 684) | <0.001 | 0.647 |
| | $V_e$ × 10⁻³ | 31181 | 236 | (212, 260) | 18491 | 273 | (233, 330) | 0.032 | 0.591 |
| | AUGC90 × 10⁻³ (mM × min) | 32027 | 215 | (186, 244) | 18696 | 322 | (293, 371) | <0.001 | 0.727 |
| Whole Gland (WG) | T2TSE (ms) | 107200 | 109 | (105, 113) | 22202 | 96 | (92, 101) | <0.001 | 0.613 |
| | TIDESPOT (ms) | 107199 | 1879 | (1769, 2034) | 22200 | 1862 | (1706, 2159) | 0.824 | 0.501 |
| | ADC × 10⁻⁶ (mm²/s) | 106507 | 1227 | (1159, 1280) | 22073 | 835 | (746, 928) | <0.001 | 0.740 |
| | $K^{Trans}$ × 10⁻³ (min⁻¹) | 102715 | 101 | (89, 111) | 21531 | 146 | (118, 173) | <0.001 | 0.662 |

TABLE 4-continued

Comparison of median parameter values between cancer and non-cancer voxels

| Model | Parameter | Non-Cancer (NC) Voxels | | | Prostate Cancer (PC) Voxels | | | p-value PCa vs. Non-PCa | AUC |
|---|---|---|---|---|---|---|---|---|---|
| | | N | Median | 95% CI | N | Median | 95% CI | | |
| | $k_{ep} \times 10^{-3}$ (min$^{-1}$) | 98387 | 387 | (352, 418) | 21255 | 551 | (480.9, 641) | <0.001 | 0.661 |
| | $V_e \times 10^{-3}$ | 98548 | 275 | (253, 307) | 21261 | 262 | (231, 306) | 0.434 | 0.475 |
| | AUGC90 $\times 10^{-3}$ (mM $\times$ min) | 102705 | 225 | (205, 254) | 21523 | 313 | (264, 352) | <0.001 | 0.643 |

The voxel-wise analyses of the n-parameter multiparametric models produced by model generation module 22 are given in Table 5. The multiparametric models generated by model generation module 22 in accordance with the techniques described herein enabled an improved AUC and S90 for the PZ pool regardless of the number of parameters. The PZ-model with four parameters, which included ADC, AUGC90, kep and T2TSE resulted in the maximum AUC and S90, compared to ADC alone with an AUC of 0.850 (vs. 0.82 for ADC, p-value=0.010) and an S90 of 0.65 (vs. 0.60 for ADC, p-value=0.063). For the WG pool, the multiparametric model resulted in an improved AUC and S90 for ≥3 parameters. Of the WG-models, the four parameter model consisting of ADC, kep, AUGC90 and Ktrans, performed the best with an AUC of 0.771 (vs. 0.742 for ADC; p=0.043) and an S90 of 0.427 (vs. 0.34 for ADC, p-value=0.101).

TABLE 5

Area under the ROC curve (AUC) and ROC (0.1) (sensitivity corresponding to 90% specificity) for combinations of MRI parameters

| Model | Parameters | AUC | 95% CI | p-value ADC vs. Model | S90 | 95% CI | p-value ADC vs. Model |
|---|---|---|---|---|---|---|---|
| Peripheral Zone (PZ-Model) | ADC Alone | 0.82 | (0.77, 0.87) | — | 0.60 | (0.46, 0.72) | — |
| | ADC + AUGC90 | 0.83 | (0.74, 0.89) | 0.299 | 0.62 | (0.32, 0.75) | 0.47 |
| | Above + $k_{ep}$ | 0.83 | (0.78, 0.90) | 0.057 | 0.63 | (0.43, 0.79) | 0.193 |
| | Above + T2TSE | 0.85 | (0.80, 0.91) | 0.010 | 0.65 | (0.51, 0.80) | 0.063 |
| | Above + K$^{Trans}$ | 0.84 | (0.81, 0.91) | 0.006 | 0.64 | (0.54, 0.80) | 0.04 |
| Whole Gland (WG-Model) | ADC Alone | 0.74 | (0.68, 0.80) | — | 0.33 | (0.19, 0.48) | — |
| | ADC + $k_{ep}$ | 0.72 | (0.51, 0.81) | 0.864 | 0.25 | (0.08, 0.44) | 0.85 |
| | Above + AUGC90 | 0.78 | (0.69, 0.84) | 0.138 | 0.44 | (0.26, 0.57) | 0.153 |
| | Above + K$^{Trans}$ | 0.77 | (0.73, 0.84) | 0.043 | 0.43 | (0.30, 0.57) | 0.101 |
| | Above + T2TSE | 0.77 | (0.72, 0.84) | 0.060 | 0.42 | (0.28, 0.57) | 0.132 |

In general, multiple individual qMR parameters showed significant differences between cancer and non-cancer with the apparent diffusion coefficient (ADC) parameter being a most significant parameter with, in one example, having an area under the receiver operating characteristic curve (AUC) of 0.82 for the PZ and 0.74 for the WG analysis. Co-registered correlative histopathology data may be used as the ground truth for development of quantitative mpMRI models for PCa detection. CBS values outperform single qMR parameter estimates for detection and may provide quantitative and user-independent identification of PCa over the whole gland. Experimental results demonstrated that a four parameter PZ-Model (AUC=0.85) and a 4 parameter WG-Model (AUC=0.77) outperforming ADC alone (p=0.010 and p=0.043, respectively).

FIGS. 5A-5D are a set of graphics showing the receiver operator characteristics curves (ROC) for the PZ-Model and the WG-Models (Solid Curves), respectively, against the best performing single quantitative parameters, ADC (broken curve), as well as correlation plots for individual subjects comparing (c) the AUCs generated with the PZ-Model and ADC in the voxels from the PZ tissue and (d) the AUCs generated with the WG-Model and ADC in the voxels from the whole gland.

Figure 5A:
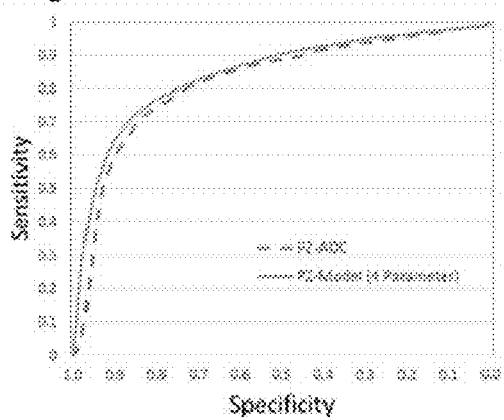
FIGS. 5A-5D are images showing the receiver operator characteristics curves (ROC) for the PZ-Model and the WG-Models (Solid Curves), respectively, against the best performing single quantitative parameters, ADC (broken curve), as well as correlation plots for individual subjects comparing (c) the AUCs generated with the PZ-Model and ADC in the voxels from the PZ tissue and (d) the AUCs generated with the WG-Model and ADC in the voxels from the whole gland.
Figure 5B:
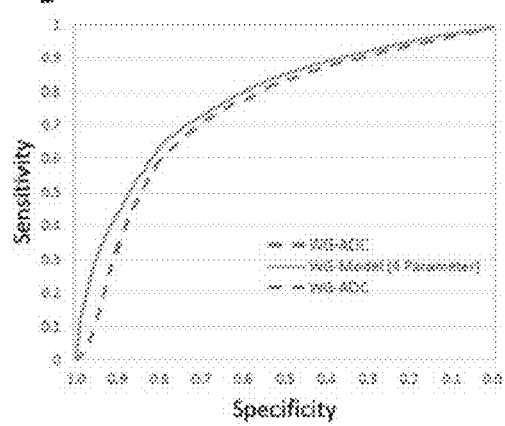
Figure 5C:
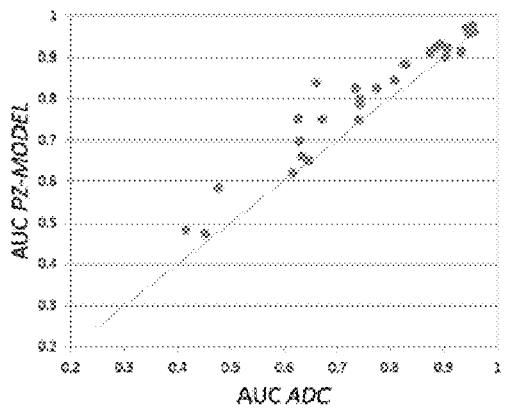
Figure 5D:
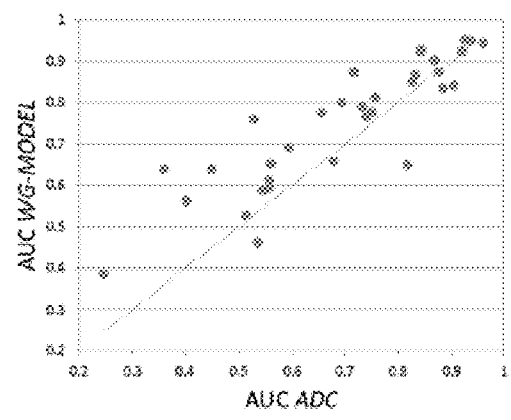
Figures 7A, 7B, 7C, 7D, 7E, 7F, 7G, 7H:
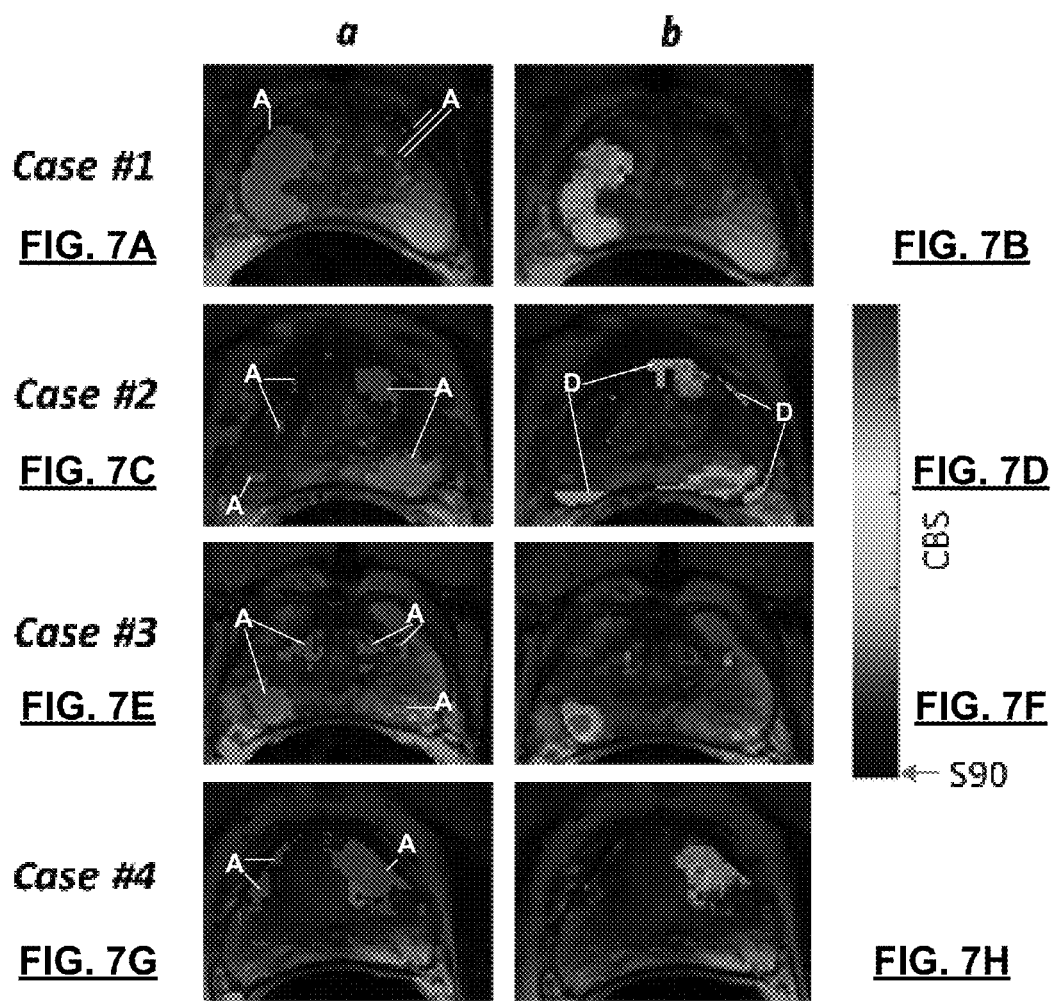
FIGS. 7A-7H are a set of images produced by a medical imaging analysis system in accordance with the techniques described herein.

Specifically, FIG. 5A and FIG. 5B show the ROC curves of ADC and the 4 parameter multiparametric models for the PZ and WG data pools, respectively. These data characterize the ability of the different models to differentiate pixels as cancer or non-cancer across all subjects in aggregate. In contrast, the correlation plots in FIGS. 5C-5D show subject-specific improvement in the AUC when going from ADC to the 4-parameter model for both the PZ and WG pools. Statistically significant improvements in AUC were observed for the 4-parameter model compared to ADC in 82% (23/28) of cases with the PZ-model and 71% (24/34) of cases with the WG-model. These are represented by the majority of patients found above the unity line in the scatter plot (FIGS. 5C-5D).

The regression coefficients estimated from the multivariate regression models may be used to calculate voxel-wise CBS scores. For example purposes, a four-parameter model generated by model generation module 22 is described herein because of its performance compared to all other n-parameter models for both the PZ and WG data pools. As one example, such a four-parameter CBS for the PZ model may be calculated using the following linear combination of qMR parameters:

$$CBS=2.2646-0.00015*T2TSE-0.0031*ADC+0.00064*KEP+0.0016*AUGC$$

while the CBS for the WG model may be:

$$CBS=-0.0083-0.0025*ADC-0.000036*KTRANS+0.0018*KEP+0.00039*AUGC$$

FIGS. 6A-6D are a set of images showing four example cases displaying Segmented anatomical data (column 1), Ground Truth maps of cancer from registered histopathology (column 2), thresholded CBS maps showing predicted cancer from the WG-Model (column 3) and PZ-Model (column 4) as well as thresholded ADC maps of cancer with thresholds determined from the WG data (WG ADC, column 5) and from the PZ data (PZ-ADC, column 6). The different contours in the segmented anatomic data (column 1) represent cancer (contoured regions A), non-cancer PZ (contoured regions B), and non-cancer CG (contoured regions C). The pixels within these contoured regions are used when defining the data pools used for the whole gland (WG) and peripheral zone (PZ) model construction and analyses. The Ground Truth maps of cancer (column 2) are composed of filled regions A from the Segmented anatomical data image and facilitate comparison with the predicted maps in columns 3 through 6. The goal is for the predicted cancer maps to match the Ground Truth maps as close as possible. The maps of predicted cancer (solid regions A) overlaid on the corresponding anatomic T2w in columns 3 through 6 use model specific thresholds of CBS and ADC appropriate for achieving an overall specificity of 90%. The PZ-Model was optimized on PZ data alone as were the thresholds for the PZ-Model and PZ-ADC. Compared to the Ground Truth they perform reasonably well in the PZ, however, because of the heterogeneity in the central gland these maps demonstrate poor performance in the CG. The WG-Model was optimized on WG data as were the thresholds for the WG-Model and WG-ADC. The WG-Model generated by model generation module 22 maps most closely match the location and extent of cancer shown in the Ground Truth data (column 2) with WG-ADC resulting in poorer overall sensitivity (notably Case #3).

FIGS. 6A-6D show several representative cases comparing different predictive models generated by model generation module 22 to the ground truth. The first column of FIGS. 6A-6D show the subdivision of the prostate using information from both the co-registered regions of cancer from histopathology and segmentation of the anatomic T2 weighted images. The PZ data pool includes qualifying lesions originating in the PZ zone and the non-cancer PZ data shown in regions B. The WG data pool consists of all qualifying cancer lesions originating from the PZ or CG and all non-cancer data depicted by both the regions B and C. Using a specificity of 90%, for cancer detection, thresholds for ADC and CBS in both the PZ and WG data pools can be determined. These thresholds may be applied to whole slices to observe how they perform at detecting cancer in comparison to the ground truth (i.e. mapped areas of cancer from histopathology shown in column 2 of FIGS. 6A-6D). Columns 3 through 6 of FIGS. 6A-6D show maps of detected cancer using the ADC and CBS data with the determined thresholds. The upper threshold for cancer based on ADC was $957 \times 10^{-6}$ mm$^2$/s for the PZ data pool and $700 \times 10^{-6}$ mm$^2$/s for the WG data pool. The lower thresholds for cancer based on CBS were, $-0.02078$ for the PZ data pool and $-0.79252$ for the WG data pool.

FIGS. 7A-7H are a set of images produced by visualization generation module 14 showing CBS maps from the WG-Model overlaid on the anatomic T2w images used for (a) cancer detection (regions A) and (b) as a continuous quantitative variable as proposed for use in monitoring disease progression or treatment response. Column (b) of FIGS. 7A-7H shows cancer areas as a varying grayscale of the continuous quantitative variable CBS. It should be understood that color visualizations of the CBS may also be used. The S90 limit was used as the lower threshold in both representations of the WG-Model CBS maps. Regions D in case #2b are from voxels which did not meet the goodness of fit criteria of $r>0.85$. FIGS. 7A-7H show maps of CBS as a continuous variable compared to the binary prediction maps for the WG-Model.

The techniques described in the present disclosure may provide several classifiers for prostate cancer detection using a method involving registered correlative histopathology data. By volumetrically reconstructing the digitally annotated PWM histopathology data, a system configured in accordance with the techniques described herein may determine the distribution of disease throughout the prostate. Assisted by a detailed sectioning protocol and deformable registration methods, the system may use these reassembled pathology data to identify regions of cancer and non-cancer on the qMR data. By further segmenting the anatomic imaging data, the system may construct models focusing on cancer detection in the PZ alone, or over the whole gland (i.e. everything within the prostatic capsule). In some examples, the constructed models can be evaluated against individual qMR parameters for validation. A system configured in accordance with the techniques of the present disclosure may generate visualizations, based on one or more constructed models, that indicate predicted PCa to users.

In some examples, using a multiparametric approach may provide advantages when compared against ADC, the single most predictive parameter. Despite statistically significant improvements with the PZ-Model ($p=0.008$) and nearly significant performance improvements in the WG-Model ($p=0.052$) when observed over all data in aggregate, it may be difficult to compare the practical impact of the different models for detecting or determining the distribution and extent of disease. In many individual cases, the advantages of including additional data beyond ADC may not be readily apparent. However, when looking at subject-specific model performance (e.g., as shown in FIGS. 5C-5D, as well as FIGS. 6A-6D) there may be individual cases where the multi-parametric models can substantively improve cancer detection and minimize false-positives. FIGS. 6A-6D show multiple cases where the regions of cancer originate from a single focus in the PZ (E.g., case 1), multiple PZ and CG foci (E.g., cases 2-3) and a single CG focus (E.g., case 4). For these cases, the WG-Model CBS most consistently identifies cancer locations and extent as evaluated by comparing with the ground truth maps. The other models occasionally miss disease (E.g., case 3: WG-ADC), underestimate disease (E.g., case 1: WG-ADC), or overestimate disease (E.g., case 4: PZ-Model, WG-ADC, PZ-ADC). One advantage of the WG-Model and WG-ADC, is that they can be applied to the whole prostate without segmentation. However, because of the heterogeneity of ADC in the central gland, the threshold to maintain a given specificity may drop from $957 \times 10^{-6}$ mm$^2$/s to $700 \times 10^{-6}$ mm$^2$/s when moving from a PZ to a WG focus. By combining ADC with multiple pharmacokinetic parameters, kep, AUGC90 and $K^{Trans}$, the performance can be improved again with the combined effect of improving cancer detection in the CG and PZ while reducing false positives mainly arising from structures in the CG. It should be noted that not all regions of cancer displayed in the ground truth maps were contained within lesions used in model development and threshold determination as they were associated with lesions smaller than 0.2 cm$^3$. However, some of these smaller foci of cancer are still identified in the detection maps in columns 3-6 of FIGS. 6A-6D.

The techniques described herein develop and apply one or more registration frameworks to map post-prostatectomy tissue onto MRI for mpMRI model development. By using such registration frameworks, classification of mpMRI voxels as cancer or non-cancer may reduce user bias and/or ambiguity, making it possible to consider the data from the whole prostate for use in training and validating models. As a result, the heterogeneity of the cancer and non-cancer regions can be considered. This may result in improved prospective performance as the models do not need to distinguish between all cancer and all non-cancer within the whole gland. Additionally, the techniques described herein do not require the a priori identification of regions of interest on which the models are applied, yielding improved applicability. In other words, the techniques described herein present an approach where predictive mpMRI models are constructed based on the use of registered post prostatectomy histopathology. The combined characteristics of the current work are unique in that:

1. A histopathology processing workflow allows the use of non-whole mount data for model development and evaluation.
2. The pathologic ground truth is not manually mapped but deformably registered from histopathology to MM thus minimizing selection bias present in manual mapping procedures.
3. The selection of non-cancer voxels is also non-subjective other than the fact that these data are derived from manual segmentation of the prostate on imaging.
4. Inclusion of all pixels from the prostate, both from cancer and non-cancer, allows the heterogeneity in both to be accommodated in the model and more closely represent the type of data a model would have to handle when applied prospectively in clinical studies.
5. A voxel-wise analysis approach is used which allows for the investigation of apparent non-coincidence of quantitative MR (qMR) parameters to be incorporated into the model development.
6. The mpMRI data used in the model is quantitative and thus may avoid the need for a qualitative assessment of the imaging data and facilitate a more immediate and voxel-wise application of the developed models.
7. Separate models are described for discriminating cancer from non-cancer in both the peripheral zone alone as well as over the whole gland.

In generating a model as described herein, imaging may be performed after biopsy, which may result in residual hemorrhage in the tissue despite the fact that the time between biopsy and imaging is maximized with practical limitations resulting from the patient's desire to be treated. Any resulting variability most likely has an effect on T2. To address any resulting variability (e.g., that may affect T2), voxels included in data pools for model development may selectively exclude regions exhibiting post biopsy hemorrhage based on calculated T1 values. In such instance, however, the impact of prospectively applying the models generated in this manner on data with post biopsy effects should be minimized. ADC may perform well as an individual parameter because it is somewhat immune to the presence of post biopsy hemorrhage. Model generation may be improved by taking into account anatomic and structural considerations that an experienced radiologist would be able to recognize, including the well-defined nature of nodules of stromal hyperplasia or the "smudged charcoal" appearance of cancer in the central gland. For instance, additional parameters may be added to the predictive models such as previously demonstrated structural features derived from the T2w anatomic data.

In some examples, additional consideration may be given to the registration procedures and cancer subtypes obtained from the enrolled patient population as used in model generation. For instance, regarding the registration procedures, there may be no assumptions about the coincidence of slice locations between imaging and histopathology and user interaction may not be involved in defining internal structures for guiding the deformable registration methods. While prone to some error and user variability these are arguably less biased than other methods proposed in the literature for using correlative histopathology for mpMRI model development. In some examples, a specific model for detecting central gland cancer alone may be constructed, in additional to and/or alternatively to pooling all cancer together in the WG-Model and WG-ADC evaluations. However, even in the absence of a CG specific model, the WG predictors can perform quite well at identifying the CG cancer foci in the cases presented in FIGS. 6A-6D.

As illustrated above, a four-parameter PZ-Model generated by module generation module 22 may show significant improvement over ADC alone. Furthermore, the WG-Model may also provide a good option in terms of its prospective use as it could be applied to the whole prostate without the need for anatomic segmentation of the gland. If segmentation is feasible, FIGS. 6A-6D provide evidence that further improvements may result in detecting and defining the extent of disease through the use of regions specific models. Independent of the model or models are used, systems configured in accordance with the techniques described herein may, in some examples, perform registration of the multiple qMRI datasets prior to performing voxel-wise classification. The system may perform such registration in an automated fashion, such as by using library based methods.

In some examples, a threshold is applied to the maps of CBS in order to detect prostate cancer with a specified sensitivity of 90% (i.e. S90). It some examples, rather than a fixed threshold, a cutoff with a defined sensitivity and specificity, optimized for the application of interest (i.e. guiding biopsy, targeting focal therapy) may be used to detect disease and define its extent. Additionally, CBS may be used as a continuous variable for quantitatively monitoring patients on active surveillance or post therapy. FIGS. 7A-7H show color maps of continuous CBS data above the S90 detection threshold. Following men longitudinally may be possible using these quantitative maps, where cancer growth could be indicated both by increasing extent exceeding the threshold and by increasing CBS value. By using CBS maps in this manner, the techniques described herein may provide a promising alternative to the standard experience-dependent, qualitative evaluation of mpMRI data.

Models generated and applied in accordance with the techniques described herein may provide potential clinical utility in various ways. For instance, potential synergies may exist when this model is used not alone, but as another tool for the radiologist interpreting mpMRI of the prostate.

The present disclosure presents a process for generating critical correlative histopathology for developing predictive models from voxel-wise mpMRI data based on mapping regions of disease from assembled histopathology to in vivo MRI. The models generated from these data show improved performance over single quantitative MRI parameters for detection. The generation of composite biomarker score (CBS) maps has the potential to improve the use of mpMRI in the management of prostate cancer by setting a base level of accuracy for all patients that is not dependent on the local radiologist expertise. That is, generating visualizations of predicted prostate cancer using models generated in accordance with the techniques described herein may yield increased accuracy in diagnoses and increased overall patient care.

Figure 8:
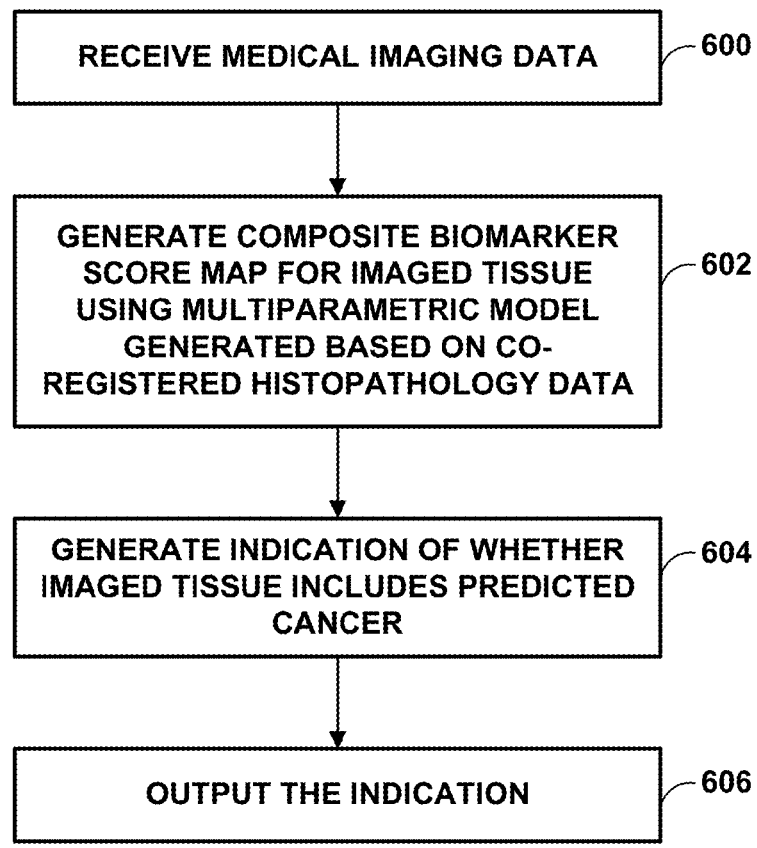
FIG. 8 is a flow chart illustrating example operations for providing predicted prostate cancer visualizations in accordance with one or more techniques of the present disclosure.

FIG. 8 is a flow chart illustrating example operations for providing predicted prostate cancer visualizations in accordance with one or more techniques of the present disclosure. For purposes of illustration only, the example operations of FIG. 8 are described below within the context of FIGS. 1 and 2.

In the example of FIG. 8, a computing system, such as system 10 of FIG. 1 (e.g., running on system 500 of FIG. 2) may receive medical imaging data (600). For instance, system 10 may receive medical imaging data from a medical imaging device, such as an MII, or from another computing device or may generate the medical imaging data using, for example, MII modality 13. The medical imaging data may include a first parametric map that maps the imaged tissue using values of a first parameter and a second parametric map that maps the imaged tissue using values of a second parameter.

System 10, in the example of FIG. 8, generates at least one composite biomarker score (CBS) for the imaged tissue using a multiparametric model (602). For instance, system 10 may generate a CBS map for the imaged tissue. The multiparametric model may be generated by system 10 as described herein based on co-registered histopathology data. In some examples, the multiparametric model may include a first coefficient corresponding to the first parameter and a second coefficient corresponding to the second parameter. The first coefficient and second coefficient are determined based on the co-registered histopathology data.

Based on the at least one CBS, system 10 generates an indication of which imaged tissue, if any, is predicted to contain cancer (604). For instance, visualization generation module 14 of system 10 may generate an overlay visualization that shows regions of the imaged tissue that, according to the model, are likely cancer. System 10 may output the indication for display or to other computer devices (606). In various examples, system 10 may output the indication for display or for storage or other analysis.

Figure 9:
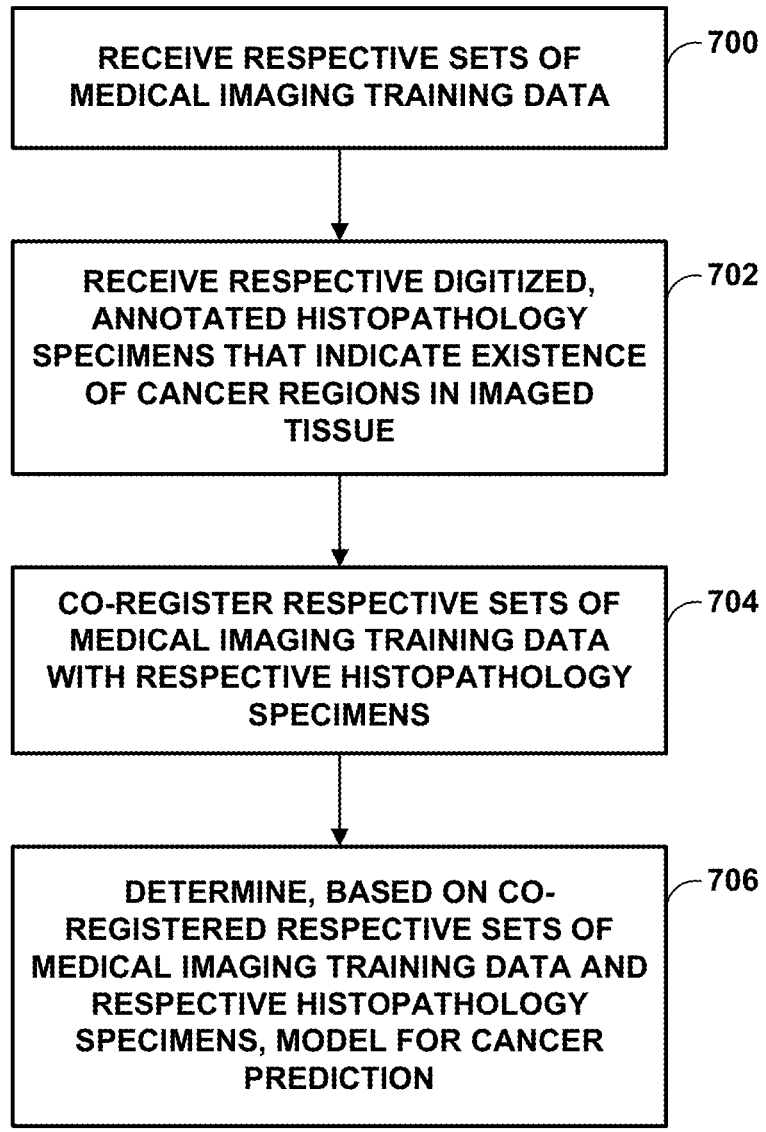
FIG. 9 is a flow chart illustrating example operations for generating a multiparametric model for cancer prediction using co-registered histopathology data in accordance with one or more techniques of the present disclosure.

FIG. 9 is a flow chart illustrating example operations for generating a multiparametric model for cancer prediction using co-registered histopathology data in accordance with one or more techniques of the present disclosure. For purposes of illustration only, the example operations of FIG. 9 are described below within the context of FIGS. 1 and 2.

In the example of FIG. 9, a computing system, such as system 10 of FIG. 1 (e.g., running on system 500 of FIG. 2) may receive respective sets of medical imaging training data (700). For instance, the medical imaging training data may be collected from a number of consenting patients. System 10 may also receive respective digitized, annotated histopathology specimens that indicate the existence of cancer regions in the imaged tissue (702). As one example, the histopathology specimens may be prepared and/or annotated by a professional and provided to system 10.

System 10, in the example of FIG. 9, may co-register the respective sets of medical imaging training data with the respective histopathology specimens (704). For instance, system 10 may co-register the histopathology data using Local Affine Transformations guided by Internal Structures (LATIS). Based on the co-registered respective sets of medical imaging training data and respective histopathology specimens, system 10 may determine a model for cancer prediction (706). The model, in some examples, may include a plurality of coefficients for respective parameters obtainable through medical imaging of tissue. That is, the model may be usable to analyze imaged tissue and predict whether the imaged tissue includes cancer.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media, which includes any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable storage medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Further examples are provided in the Appendix attached below and incorporated herein by reference.

Various examples have been described. These and other examples are within the scope of the following claims.

What is claimed is:

1. A method comprising:
receiving, by a computing device, a first parametric map that maps imaged tissue of a patient using values of a first parameter, and a second parametric map that maps the imaged tissue using values of a second parameter, wherein the first parametric map and the second parametric map are generated from medical imaging data for the imaged tissue;
applying, by the computing device, a multiparametric model to the first parametric map and the second parametric map to generate a Composite Biomarker Score (CBS) map that maps the imaged tissue using a respective CBS value for one or more voxels of the imaged tissue, wherein the multiparametric model specifies a multiparametric operation based on at least the first parameter and the second parameter that is based on co-registered histopathology data and respective sets of medical imaging training data;
determining, by the computing device, locations of the CBS map that correspond to CBS values that satisfy a threshold;
generating, by the computing device, a visual indication of the determined locations of the CBS map as regions of the imaged tissue predicted to include cancer; and
outputting, by the computing device, the visual indication.

2. The method of claim 1, wherein generating the visual indication comprises generating the locations of the CBS map that correspond to the CBS values that satisfy the threshold as an overlay image for the medical imaging data for the imaged tissue, and wherein outputting the indication comprises outputting, for display, the overlay image.

3. The method of claim 1, wherein determining the locations of the CBS map that correspond to the CBS values that satisfy the threshold comprises determining locations of the CBS map that correspond to the CBS values that are greater than a first CBS value and less than a second CBS value.

4. The method of claim 1, further comprising receiving a third parametric map that maps the imaged tissue using values of a third parameter, and a fourth parametric map that maps the imaged tissue using values of a fourth parameter, wherein the third parametric map and the fourth parametric map are generated from the medical imaging data for the imaged tissue, and wherein the multiparametric model comprises:
a first coefficient corresponding to the first parameter;
a second coefficient corresponding to the second parameter;
a third coefficient corresponding to a third parameter; and
a fourth coefficient corresponding to a fourth parameter, and wherein each of the first coefficient, second coefficient, third coefficient and fourth coefficient are a function of the co-registered histopathology data.

5. The method of claim 1, wherein the co-registered histopathology data is registered to the respective sets of medical imaging training data using Local Affine Transformations guided by Internal Structures (LATIS).

6. The method of claim 1, wherein each of the first parameter and the second parameter comprises one of: an apparent T2 (T2) parameter, an apparent diffusion coefficient (ADC) parameter, a first pharmacokinetic parameter $K^{Trans}$, a second pharmacokinetic parameter $k_{ep}$, or an area under the gadolinium concentration time curve over 90 s (AUGC90) parameter.

7. The method of claim 1, wherein the medical imaging data corresponding to the imaged tissue comprises medical imaging data corresponding to at least a portion of a prostate gland.

8. The method of claim 1, wherein the multiparametric model is generated to predict cancer specifically in at least one of: a particular prostate region, a particular prostate zone, or a whole prostate gland.

9. The method of claim 1, wherein the medical imaging data comprises magnetic resonance imaging (MRI) data.

10. A method comprising:
receiving, by a computing device, respective sets of training data corresponding to imaged tissue of a plurality of patients, wherein each respective set of training data comprises a first parametric map that maps imaged tissue of a respective patient using values of a first parameter, and a second parametric map that maps the imaged tissue using values of a second parameter, and wherein the first parametric map and the second parametric map are generated based on a respective set of medical imaging data for the imaged tissue;
receiving, by the computing device, respective digitized, annotated histopathology specimens that indicate the existence of cancer regions in the imaged tissue;
co-registering, by the computing device, the respective sets of training data with the respective histopathology specimens;
determining, by the computing device and based on the co-registered respective sets of training data and respective histopathology specimens, a model for cancer prediction, wherein the model comprises a multiparametric operation based on at least the first parameter and the second parameter;
receiving medical imaging testing data corresponding to tissue of a patient;
calculating, using the model for cancer prediction, at least one Composite Biomarker Score (CBS) for the medical imaging testing data; and
generating, based on the at least one CBS, an indication of whether the tissue of the patient is predicted to include cancer.

11. The method of claim 10, wherein the respective digitized, annotated histopathology specimens are generated by:
excising the imaged tissue;
sectioning the imaged tissue into sections in accordance with planes of the respective set of training data;
digitizing the sections; and
annotating the digitized sections.

12. The method of claim 10, wherein co-registering the respective sets of training data with the respective histopathology specimens comprises registering the respective histopathology specimens to the respective sets of training data using Local Affine Transformations guided by Internal Structures (LATIS).

13. The method of any of claim 10, wherein each of the first parameter and the second parameter comprises one of: an apparent T2 (T2) parameter, an apparent diffusion coefficient (ADC) parameter, a first pharmacokinetic parameter $K^{Trans}$, a second pharmacokinetic parameter $k_{ep}$, or an area under the gadolinium concentration time curve over 90 s (AUGC90) parameter.

14. The method of claim 10, wherein the model is generated to predict cancer specifically in at least one of: a particular prostate region, a particular prostate zone, or a whole prostate gland.

15. A medical imaging analysis device comprising:
a non-transitory computer-readable storage medium storing a first parametric map that maps imaged tissue of a patient using values of a first parameter, and a second parametric map that maps the imaged tissue using values of a second parameter, wherein the first parametric map and the second parametric map are generated from medical imaging data for the imaged tissue; and
a processor coupled to the computer-readable storage medium;
wherein the processor is configured to:
apply a multiparametric model to the first parametric map and the second parametric map to generate a Composite Biomarker Score (CBS) map that maps the imaged tissue using a respective CBS value for one or more voxels of the imaged tissue, wherein the multiparametric model specifies a multiparametric operation based on at least the first parameter and the second parameter that is based on co-registered histopathology data and respective sets of medical imaging training data;
determine locations of the CBS map that correspond to CBS values that satisfy a threshold;
generate, a visual indication of the locations of the CBS map that correspond to CBS values that satisfy the threshold as regions predicted to include cancer; and
output the indication.

16. The medical imaging analysis device of claim 15, wherein the processor is configured to:
generate the visual indication by generating the visual indication as an overlay image for the medical imaging data for the imaged tissue; and
output the overlay image for display.

17. The medical imaging analysis device of claim 15, wherein the processor is configured to determine the locations of the CBS map that correspond to CBS values that satisfy the threshold by identifying locations of the CBS map that correspond to CBS values that are greater than a first CBS value and less than a second CBS value.

18. The medical imaging analysis device of claim 15, wherein the medical imaging analysis device comprises one of a computer, a laptop, a mobile device, a server or a medical imaging system having an input modality.

* * * * *